United States Patent
Coutable et al.

(10) Patent No.: US 12,133,461 B2
(45) Date of Patent: Oct. 29, 2024

(54) ORGANIC SEMICONDUCTOR COMPOUND HAVING AN INDOL GROUP, ORGANIC OPTOELECTRONIC COMPONENT COMPRISING SUCH A COMPOUND

(71) Applicant: HELIATEK GMBH, Dresden (DE)

(72) Inventors: Ludovic Coutable, Ulm (DE); Olga Gerdes, Ulm (DE); Dirk Hildebrandt, Ulm (DE); Martin Pfeiffer-Jacob, Dresden (DE); Nina Grimm, Ulm (DE)

(73) Assignee: HELIATEK GMBH, Dresden (DE)

( * ) Notice: Subject to any disclaimer, the term of this patent is extended or adjusted under 35 U.S.C. 154(b) by 216 days.

(21) Appl. No.: 17/630,932

(22) PCT Filed: Jul. 24, 2020

(86) PCT No.: PCT/DE2020/100662
§ 371 (c)(1),
(2) Date: Jan. 28, 2022

(87) PCT Pub. No.: WO2021/018351
PCT Pub. Date: Feb. 4, 2021

(65) Prior Publication Data
US 2022/0320443 A1    Oct. 6, 2022

(30) Foreign Application Priority Data
Jul. 29, 2019 (DE) .................. 10 2019 120 457.7

(51) Int. Cl.
*H10K 85/60* (2023.01)
*C07D 405/14* (2006.01)
*H10K 30/30* (2023.01)

(52) U.S. Cl.
CPC ....... *H10K 85/6572* (2023.02); *C07D 405/14* (2013.01); *H10K 85/653* (2023.02); *H10K 30/30* (2023.02)

(58) Field of Classification Search
CPC .. H10K 85/6572; H10K 85/653; H10K 30/30; H10K 85/654; H10K 30/50; C07D 405/14; Y02E 10/549
See application file for complete search history.

(56) References Cited

U.S. PATENT DOCUMENTS

2007/0090371 A1    4/2007 Drechsel
2019/0006599 A1*   1/2019 Hildebrandt ......... C07D 405/14
2019/0019957 A1    1/2019 Hildebrandt

FOREIGN PATENT DOCUMENTS

DE    102004014046 A1    9/2004
WO    WO 2011161108 A1   12/2011
(Continued)

OTHER PUBLICATIONS

Yuka Matsuda et al. "Formal [4+2] Reaction between 1.3-Diynes and Pyrroles: Gold(I)-Catalyzed Indole Synthesis by Double Hydroarylation", Chemistry—A European Journal, vol. 21, No. 4, Nov. 2014, p. 1463-1467, Wiley-VCH Verlag GmbH, Weinheim, Germany.

(Continued)

*Primary Examiner* — Angelo Trivisonno
(74) *Attorney, Agent, or Firm* — LEYDIG, VOIT & MAYER, LTD.

(57) ABSTRACT

A compound of the general formula I

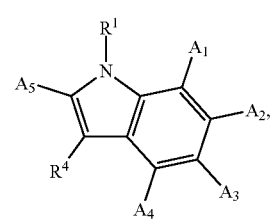

wherein R1 is selected from the group consisting of H, alkoxy, alkyl, fluorinated alkyl, partly fluorinated alkyl, and aryl; R4 is selected from the group consisting of H, halogen, CN, alkoxy, alkyl, fluorinated alkyl, partly fluorinated alkyl, branched or linear, cyclic or open-chain alkyl, amino, aryl, and alkenyl; and at least one A1, A2, A3 or A4 in each case is independently the group Ia (Continued)

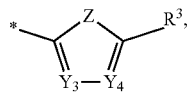

wherein each variable is as defined herein.

20 Claims, 27 Drawing Sheets

(56) References Cited

FOREIGN PATENT DOCUMENTS

| WO | WO 2017114937 A1 | 7/2017 | |
|---|---|---|---|
| WO | WO-2017114938 A1 * | 7/2017 | ............ C07D 405/14 |

OTHER PUBLICATIONS

Xiaoyan Yang et al. "A Free-standing electrochromic material of poly(5,7-bis(2-(3,4-ethylenedioxy)thienyl)-indole) and its application in electrochromic device", Journal of Polymer Science Part A: Polymer Chemistry, vol. 55, No. 14, Apr. 2017, p. 2356-2364, Wiley Publishing, Hoboken, USA.

Yanming Sun et al. "Solution-processed small-molecule solar cells with 6.7% efficiency", Nature Materials, vol. 11, No. 1, Nov. 2011, p. 44-48, Macmillan Publishers, New York City, USA.

Qin et al., "Simple Synthesis regarding novel bianchored metal free organic dyes based on indole for dye synthesized solar cells", Journal of Materials Science Materials in Electronics, Dec. 28, 2015, vol. 27(4), p. 3974-3981, Springer Science+Business Media, New York, US.

Fitzner et al., "Dicyanovinyl-Substituted Oligothiophenes: Structure-Property Relationships and Application in Vacuum-Processed Small Molecule Organic Solar Cells", Advanced Functional Materials, Jan. 27, 2011, vol. 21, p. 897-910, Wiley-VCH, Weinheim, Germany.

Lucchesini, "A simple way to sequentially connected polycycles containing terminal pyrrole rings: synthesis of possible precursors of materials for nonlinear optics", Tetrahedron, Nov. 1, 1992, vol. 48. No. 45, pp. 9951-9966, Pergamon Press Ltd, United Kingdom.

* cited by examiner

ORGANIC SEMICONDUCTOR COMPOUND HAVING AN INDOL GROUP, ORGANIC OPTOELECTRONIC COMPONENT COMPRISING SUCH A COMPOUND

CROSS-REFERENCE TO PRIOR APPLICATIONS

This application is a U.S. National Phase application under 35 U.S.C. § 371 of International Application No. PCT/DE2020/100662, filed on Jul. 24, 2020, and claims benefit to German Patent Application No. DE 10 2019 120 457.7, filed on Jul. 29, 2019. The International Application was published in German on Feb. 4, 2021 as WO 2021/018351 under PCT Article 21(2).

FIELD

The present invention relates to a compound of the general formula I, to optoelectronic components comprising such a compound, and to the use of such a compound in optoelectronic components.

BACKGROUND

Circuits made from electrically conductive polymers or small organic molecules are used in organic electronics. Organic optoelectronic components may, for example, be displays, data storage means or transistors. These components also include organic optoelectronic components, especially organic photoactive components, especially solar cells and photodetectors that have a photoactive layer in which incident electromagnetic radiation results in the generation of charge carriers, particularly bound electron-hole pairs (excitons).

Photoactive optoelectronic components enable the conversion of electromagnetic radiation into electrical current by making use of the photoelectric effect. A conversion of electromagnetic radiation of this kind requires absorber materials that show good absorption properties. Further optoelectronic components are light-emitting electroluminescent components that emit light when electrical current flows through them. Optoelectronic components comprise at least two electrodes, with one electrode applied to a substrate and the other functioning as counterelectrode. Between the electrodes is at least one photoactive layer, preferably an organic photoactive layer. Further layers, for example charge carrier transport layers, can additionally be arranged between the electrodes.

Numerous absorber materials for organic solar cells are known from the prior art.

International patent application WO2017114937A1 discloses an organic compound, the organic compound being characterized by high absorption in the short-wave spectral range of visible light. The use of this compound for an organic electronic component and a method for preparing the compound are also disclosed.

International patent application WO2017114938A1 discloses an organic semiconducting material and the use thereof in organic components, wherein the organic material can serve as a functional component in organic electronic components, resulting in improved absorption in organic solar cells, or has increased charge carrier mobility.

Although the absorber materials disclosed in the prior art are suitable for photoactive layers in organic solar cells, the efficiency of the absorber materials is in need of improvement, especially in order to make organic solar cells (OPVs) competitive with conventional silicon-based solar cells. A particular disadvantage from the prior art is the inadequate efficiency of absorber materials, especially in the blue/green region of visible light, with a high absorption coefficient, especially for construction of solar cells with an open-circuit voltage Uoc in the region of 0.9 V or more, preferably in the region of 0.94 V or more, or preferably in the region of 0.95 V or more, especially in the region of 1 V. In particular, at wavelengths in the region of 500-600 nm, the absorption of known organic compounds of small molecules, especially absorber molecules, for organic optoelectronic components is inadequate. The effect of this is that the photons in this wavelength range cannot be utilized to a sufficient degree.

There is a continuing search for semiconductor organic materials which, when used in organic optoelectronic components, lead to an improvement in the properties of these components, especially in absorption of electromagnetic radiation.

SUMMARY

In an aspect, provided is a compound of the general formula I

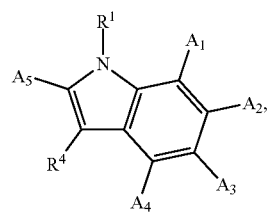

wherein
R1 is selected from the group consisting of H, alkoxy, alkyl, fluorinated alkyl, partly fluorinated alkyl, and aryl;
R4 is selected from the group consisting of H, halogen, CN, alkoxy, alkyl, fluorinated alkyl, partly fluorinated alkyl, branched or linear, cyclic or open-chain alkyl, amino, aryl, and alkenyl;
at least one A1, A2, A3 or A4 in each case is independently the group Ia

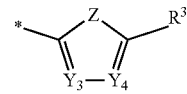

where, in each case, * denotes the attachment to the compound of the general formula I;
Z is selected from the group consisting of O, S, Se, and N—R8 where R8 is selected from the group consisting of H, alkoxy, alkyl, fluorinated alkyl, partly fluorinated alkyl, and aryl;
Y3 is N or C—R9 where R9 is selected from the group consisting of H, halogen, alkoxy, branched or linear, cyclic or open-chain alkyl, alkenyl, and aryl, wherein H may in each case be substituted;
Y4 is N or C—R10 where R10 is selected from the group consisting of H, halogen, alkoxy, branched or linear, cyclic or open-chain alkyl, alkenyl, and aryl, wherein H may in each case be substituted;

where R9 and R10 may be bonded homocyclically or heterocyclically to one another in the form of a ring structure; and R3 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double bond, wherein H may be substituted by CN or F;

the other A1, A2, A3 or A4 are each independently selected from the group consisting of H, halogen, CN, alkoxy, alkyl, fluorinated alkyl, partly fluorinated alkyl, and amino; and A5 is selected from the group consisting of H, alkyl, alkoxy and the group Ib

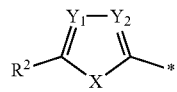

where * denotes the attachment to the compound of the general formula I;

X is selected from the group consisting of O, S, Se, and N—R7, where R7 is selected from the group consisting of H, alkoxy, alkyl, fluorinated alkyl, partly fluorinated alkyl, and aryl;

Y1 is N or C—R5 where R5 is selected from the group consisting of H, halogen, alkoxy, branched or linear, cyclic or open-chain alkyl, alkenyl, and aryl, wherein H may in each case be substituted;

Y2 is N or C—R6 where R6 is selected from the group consisting of H, halogen, alkoxy, branched or linear, cyclic or open-chain alkyl, alkenyl, and aryl, wherein H may in each case be substituted;

where R5 and R6 may be bonded homocyclically or heterocyclically to one another in the form of a ring structure; and R2 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double bond, wherein H may be substituted by CN or F.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
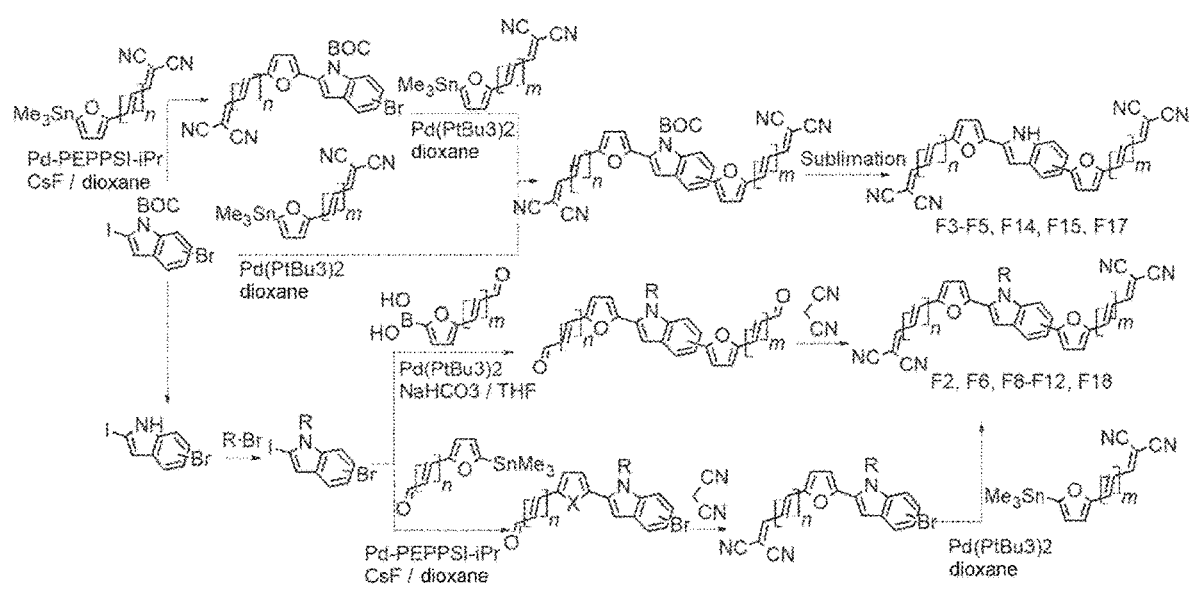
FIG. 1 a working example of a synthesis scheme for synthesis of compounds of the invention.

It is therefore an object of the invention to provide organic compounds having improved absorption properties that are suitable for use in organic optoelectronic components, an optoelectronic component comprising at least one such compound, and for the use of such compounds in an optoelectronic component, where the disadvantages mentioned do not occur, and where, in particular, the absorption of electromagnetic radiation is improved and/or the efficiency of organic solar cells is increased.

The object is achieved by the subject matter of the independent claims. Advantageous embodiments are apparent from the dependent claims.

The object is, in particular, achieved in that a compound of the general formula I is provided

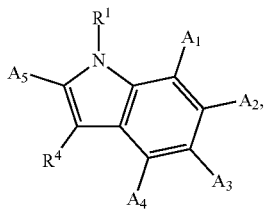

characterized in that
R1 is selected from the group consisting of H, alkoxy, alkyl, fluorinated alkyl, partly fluorinated alkyl, and aryl;
R4 is selected from the group consisting of H, halogen, CN, alkoxy, alkyl, fluorinated alkyl, partly fluorinated alkyl, branched or linear, cyclic or open-chain alkyl, amino, aryl, and alkenyl, and an electron-withdrawing alkyl group having at least one C—C double bond, wherein H may be substituted by CN or F;
at least one A1, A2, A3 or A4 in each case is independently the group Ia

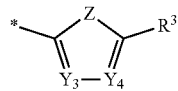

where, in each case, * denotes the attachment to the compound of the general formula I;
Z is selected from the group consisting of O, S, Se, and N—R8, where R8 is selected from the group consisting of H, alkoxy, alkyl, fluorinated alkyl, partly fluorinated alkyl, and aryl;
Y3 is N or C—R9, where R9 is selected from the group consisting of H, halogen, alkoxy, branched or linear, cyclic or open-chain alkyl, alkenyl, and aryl, wherein H may in each case be substituted;
Y4 is N or C—R10, where R10 is selected from the group consisting of H, halogen, alkoxy, branched or linear, cyclic or open-chain alkyl, alkenyl, and aryl, wherein H may in each case be substituted; where R9 and R10 may be homocyclically or heterocyclically linked to one another in the form of a ring structure; and R3 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double bond, wherein H may be substituted by CN or F;
the other A1, A2, A3 or A4 are each independently selected from the group consisting of H, halogen, CN, alkoxy, alkyl, fluorinated alkyl, partly fluorinated alkyl, and amino; and
A5 is selected from the group consisting of H, alkyl, alkoxy and the group Ib

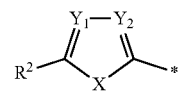

where * denotes the attachment to the compound of the general formula I;
X is selected from the group consisting of O, S, Se, and N—R7, where R7 is selected from the group consisting of H, alkoxy, alkyl, fluorinated alkyl, partly fluorinated alkyl, and aryl;
Y1 is N or C—R5, where R5 is selected from the group consisting of H, halogen, alkoxy, branched or linear, cyclic or open-chain alkyl, alkenyl, and aryl, wherein H may in each case be substituted;
Y2 is N or C—R6, where R6 is selected from the group consisting of H, halogen, alkoxy, branched or linear, cyclic or open-chain alkyl, alkenyl, and aryl, wherein H may in each case be substituted;
where R5 and R6 may be bonded homocyclically or heterocyclically to one another in the form of a ring structure; and
R2 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double bond, wherein H may be substituted by CN or F.

The present invention relates in particular to A-D-A dyes of the compound of the general formula I, wherein the central structural unit is an indole unit. The presence of a furan or thiophene group in particular on the indole unit, and of at least one double bond on the furan or thiophene group, preferably arranged adjacent to at least one of the electron-withdrawing groups, improves the properties of the absorber materials.

In a preferred embodiment of the invention, the group Ia and/or the group Ib has at least one electron-withdrawing alkyl group having at least one C—C double bond, wherein H may be substituted by CN or F; especially preferably, the group Ia and the group Ib have at least one electron-withdrawing alkyl group having at least one C—C double bond, wherein H may be substituted by CN or F.

In a preferred embodiment of the invention, R9 and R10 are not bonded homocyclically or heterocyclically to one another in the form of a ring structure.

In a preferred embodiment of the invention, R5 and R6 are not bonded homocyclically or heterocyclically to one another in the form of a ring structure.

In a preferred embodiment of the invention, the central indole unit, especially the pyrrole ring of the indole unit, does not have any further fused aromatic system.

In a preferred embodiment of the invention, the pyrrole rings are fused units containing furan, especially benzofurans.

Substitution is understood to mean, in particular, the replacement of H by a substituent. A substituent is understood to mean, in particular, all atoms and atomic groups except hydrogen, preferably a halogen, an alkyl group, where the alkyl group may be linear or branched, an alkenyl group, an alkynyl group, an alkoxy group, a thioalkoxy group, an aryl group, or a heteroaryl group. A halogen is understood to mean, in particular, F, Cl or Br, preferably F.

In a preferred embodiment of the invention, none of the carbon atoms in an alkyl group has been replaced by a heteroatom.

In a preferred embodiment of the invention, R2 and R3 are not a hydrogen atom.

In a preferred embodiment of the invention, either A1 or A4 is not a hydrogen atom. In a particularly preferred embodiment of the invention, A1 and A4 are a hydrogen atom.

A heteroatom, especially a heteroatom in the general formula I, is understood to mean, in particular, an atom selected from the group consisting of O, S, Se, Si, B, N and P, preferably selected from the group consisting of O, S, Se and N.

In an alternatively preferred embodiment, the central indole unit, especially the pyrrole ring of the indole unit, has at least one fused homocyclic or heterocyclic ring structure.

In a preferred embodiment of the invention, the ring structure formed between R5 and R6 and/or between R9 and R10 has at least one double bond, preferably an aromatic system.

The compound of the invention is especially a small molecule. Small molecules are understood to mean, in particular, non-polymeric organic molecules having monodisperse molar masses between 100 and 2000 g/mol that exist in the solid phase at standard pressure (air pressure of the ambient atmosphere) and at room temperature. In particular, the small molecules are photoactive, "photoactive" being understood to mean that the molecules undergo a change of charge state and/or of polarization state when light is supplied. A particular feature of the photoactive molecules is an absorption of electromagnetic radiation within a defined wavelength range, with conversion of absorbed electromagnetic radiation, i.e. photons, to excitons.

In a preferred embodiment of the invention, the aryl groups and heteroaryl groups of the general formulae I, II, III, IV, V, VI, VII and/or VIII are C5-C10-aryl and C5-C10-heteroaryl groups.

In a preferred embodiment of the invention, Y1, Y2, Y3, and Y4 are each independently selected from the group consisting of N, CH, CF, C—CH$_3$, C—CF$_3$, C—C$_2$H$_5$, C—C$_3$H$_8$, C—OCH$_3$, C—OC$_2$H$_5$, C—SCH$_3$, C—SC$_2$H$_5$.

In a preferred embodiment of the invention, the cyclic or open-chain alkyl groups of the compounds of the invention are linear or branched, the alkyl groups preferably being C1-C5 alkyl groups.

In a preferred embodiment of the invention, at least one of positions Y1, Y2, 3 and Y4 is N; preferably, at least one position Y1 or Y2 is N and/or at least one position Y3 or Y4 is N. This especially achieves lowering of the highest molecular orbital occupied by electrons (HOMO), with a shift in the absorption spectrum of the compound of the invention to shorter wavelengths.

In a particularly preferred embodiment of the invention, Y1, Y2, Y3 and Y4 are each CH. In this case, the two five-membered rings are each furan rings that have further substitution or have no further substitution.

The compounds of the invention have advantages compared to the prior art. Advantageously, the compounds of the invention have surprisingly good absorption characteristics in a comparatively broad spectral range of visible light of 500-700 nm; in particular, surprisingly high absorption was observed in the spectral range of about 500-700 nm. Advantageously, absorber materials having improved absorption in a wavelength range of the blue/green region of visible light are provided. Surprisingly, the central structural unit of the compound of the invention, namely the central indole unit, is of excellent suitability for obtaining compounds having the desired absorption properties. The compounds of the invention advantageously have sufficient thermal, chemical, and electrochemical stability to meet the demands typically placed on them in the manufacture and operation of photoactive organic electronic components; in particular, these compounds can be readily evaporated under reduced pressure, especially without residue. Advantageously, the compounds of the invention have charge carrier transport properties that make them suitable for use in organic optoelectronic components, especially in organic solar cells. Advantageously, the compound has very good transport properties, especially with particularly suitable energy levels. It has been found that, surprisingly, the compounds of the invention have particularly good absorption of electromagnetic radiation, especially light in the visible spectral region, by virtue of the central structural element of the indole unit. This especially increases the efficiency of organic optoelectronic components and/or increases charge carrier mobility in photoactive layers. Advantageously, the compounds of the invention have a high coefficient of absorption. Advantageously, the open-circuit voltage Uoc is above 0.9 V, preferably above 0.94 V, especially preferably above 0.95 V.

In one development of the invention, the compound is a compound of the general formula II

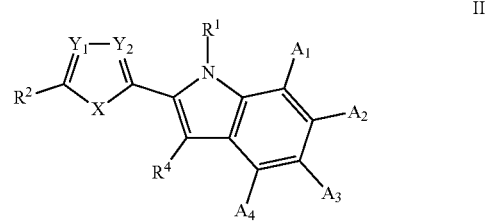

where R1 is preferably selected from the group consisting of H, methyl, ethyl, propyl, isopropyl, butyl, isobutyl and s-butyl;

R4 is preferably selected from the group consisting of H, halogen, CN, alkoxy and alkyl; and where X and Z are each independently O or S.

In one development of the invention, the compound is a compound of the general formula VII

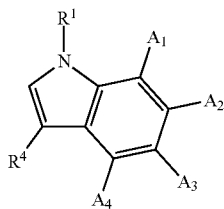

VII where R1 is preferably selected from the group consisting of H, methyl, ethyl, propyl, isopropyl, butyl, isobutyl and s-butyl;
R4 is preferably selected from the group consisting of H, halogen, CN, alkoxy and alkyl; and where Z is O or S; and where A1 or A4 is preferably a hydrogen atom.

In a preferred embodiment of the invention, at least two A1, A2, A3 or A4 are each independently the group Ia

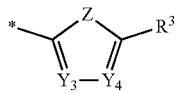

where the other A1, A2, A3 or A4 are each independently selected from the group consisting of H, halogen, CN, alkoxy, alkyl, fluorinated alkyl, partly fluorinated alkyl, and amino.

In one development of the invention, at least one A1, A2, A3 or A4 is independently a

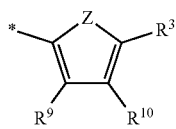

where R3 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double bond, wherein H may be substituted by CN or F; R3 is preferably an electron-withdrawing alkyl group having at least one C—C double bond, wherein H may be substituted by CN or F;
R9 is selected from the group consisting of H, halogen, alkoxy, branched or linear, cyclic or open-chain alkyl, alkenyl, and aryl, wherein H may in each case be substituted;
R10 is selected from the group consisting of H, halogen, alkoxy, branched or linear, cyclic or open-chain alkyl, alkenyl, aryl, wherein H may in each case be substituted; and where R9 and R10 may be bonded homocyclically or heterocyclically to one another in the form of a ring structure.

In a preferred embodiment of the invention, at least two of the groups A1, A2, A3 or A4 are each independently a

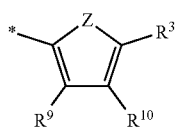

where R3 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double bond, wherein H may be substituted by CN or F; R3 is preferably an electron-withdrawing alkyl group having at least one C—C double bond, wherein H may be substituted by CN or F;
R9 is selected from the group consisting of H, halogen, alkoxy, branched or linear, cyclic or open-chain alkyl, alkenyl, and aryl, wherein H may in each case be substituted;
R10 is selected from the group consisting of H, halogen, alkoxy, branched or linear, cyclic or open-chain alkyl, alkenyl, aryl, wherein H may in each case be substituted; and where R9 and R10 may be bonded homocyclically or heterocyclically to one another in the form of a ring structure.

In one development of the invention, the compound is a compound of the general formula III and/or IV

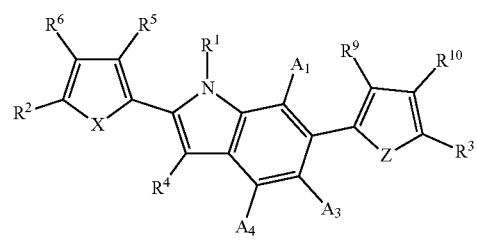

III

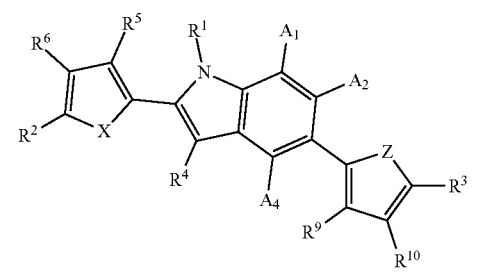

IV where R1 is H or alkyl;
X and Z are each independently O or S;
A1, A3 and A4, or A1, A2 and A4, are each independently selected from the group consisting of H, halogen, CN, alkoxy, alkyl, fluorinated alkyl, and partly fluorinated alkyl;
R3 is selected from the group consisting of H, alkyl, fluorinated alkyl, partly fluorinated alkyl, alkoxy, amino, aryl, and an electron-withdrawing alkyl group having at least one C—C double bond, wherein H may be substituted by CN or F; R3 is preferably an electron-withdrawing alkyl group having at least one C—C double bond, wherein H may be substituted by CN or F; and
where, preferably, X and Z are O, R4 is H, and R5 and R6 are H.

In a preferred embodiment of the invention, the compound is a compound of the general formula X

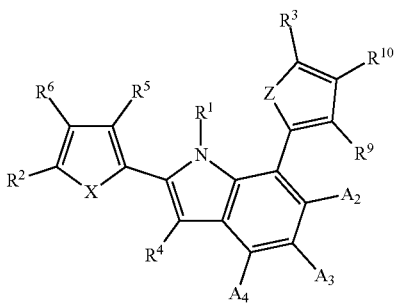

where R1 is H or alkyl;
X and Z are each independently O or S;
A2, A3 and A4 are each independently selected from the group consisting of H, halogen, CN, alkoxy, alkyl, fluorinated alkyl, and partly fluorinated alkyl;
R3 is selected from the group consisting of H, alkyl, fluorinated alkyl, partly fluorinated alkyl, alkoxy, amino, aryl, and an electron-withdrawing alkyl group having at least one C—C double bond, wherein H may be substituted by CN or F; R3 is preferably an electron-withdrawing alkyl group having at least one C—C double bond, wherein H may be substituted by CN or F; and
where, preferably, X and Z are O, R4 is H, and R5 and R6 are H.

In a preferred embodiment of the invention, in the compound of the general formula X, A2, A3 and A4 are each H.

In a preferred embodiment of the invention, the compound is a compound of the general formula XI where, preferably, X and Z are O, R4 is H, and R5 and R6 are H.

In a preferred embodiment of the invention, in the compound of the general formula XI, A1, A2 and A3 are each H.

In a preferred embodiment of the invention, the compound of the general formula I has an N at position Y1 and/or Y2 in formula Ia and at position Y3 and/or Y4 in formula IIa

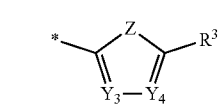

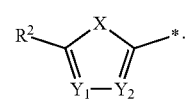

Thereby, in particular, the resultant optical properties, especially the absorption of light, are more favorable than in the case of comparable compounds having an atom other than O.

In one development of the invention, in formula III, A1, A3 and A4 are H (formula V), and, in formula IV, A1, A2 and A4 are H (formula VI),

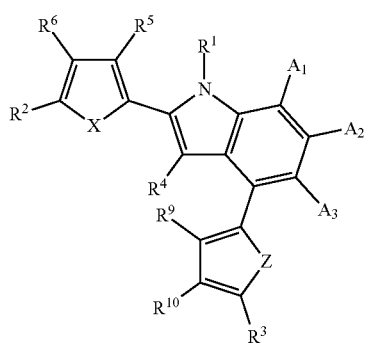

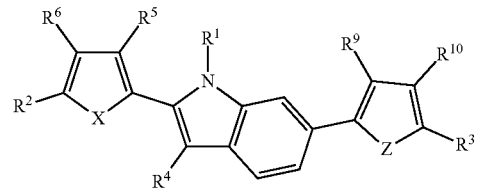

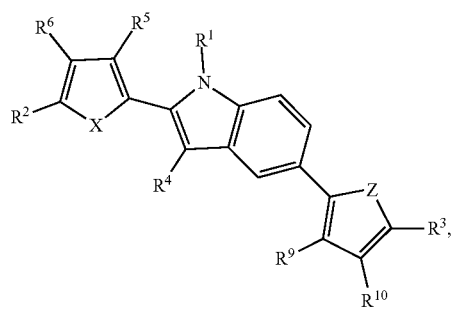

where X and Z are each independently O or S, where R5 and R6 are preferably H. This realizes the advantageous effects of the present invention in an exceptional manner.

In one development of the invention, the compound is a compound of the general formula VIII and/or IX

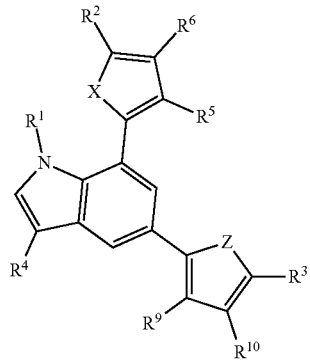

VIII

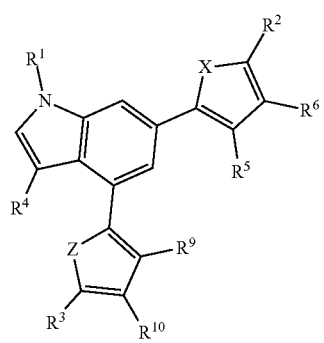

IX where R1 is H or alkyl;

X and Z are each independently O or S;

R9 is selected from the group consisting of H, halogen, alkoxy, branched or linear, cyclic or open-chain alkyl, alkenyl, aryl, wherein H may in each case be substituted;

R10 is selected from the group consisting of H, halogen, alkoxy, branched or linear, cyclic or open-chain alkyl, alkenyl, aryl, wherein H may in each case be substituted, and where R9 and R10 may be bonded homocyclically or heterocyclically to one another in the form of a ring structure;

R5 is selected from the group consisting of H, halogen, alkoxy, branched or linear, cyclic or open-chain alkyl, alkenyl, aryl, wherein H may in each case be substituted;

R6 is selected from the group consisting of H, halogen, alkoxy, branched or linear, cyclic or open-chain alkyl, alkenyl, aryl, wherein H may in each case be substituted, and where R5 and R6 may be bonded homocyclically or heterocyclically to one another in the form of a ring structure; and where, preferably, R5 and R6 are H and R9 and R10 are H.

In a preferred embodiment of the invention, the compound is a compound of the general formula XII

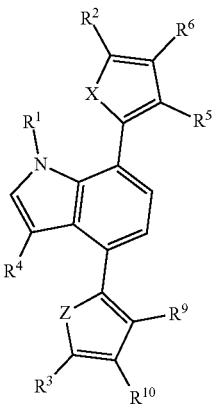

XII where R1 is H or alkyl;

X and Z are each independently O or S;

R9 is selected from the group consisting of H, halogen, alkoxy, branched or linear, cyclic or open-chain alkyl, alkenyl, aryl, wherein H may in each case be substituted;

R10 is selected from the group consisting of H, halogen, alkoxy, branched or linear, cyclic or open-chain alkyl, alkenyl, aryl, wherein H may in each case be substituted, and where R9 and R10 may be bonded homocyclically or heterocyclically to one another in the form of a ring structure;

R5 is selected from the group consisting of H, halogen, alkoxy, branched or linear, cyclic or open-chain alkyl, alkenyl, aryl, wherein H may in each case be substituted;

R6 is selected from the group consisting of H, halogen, alkoxy, branched or linear, cyclic or open-chain alkyl, alkenyl, aryl, wherein H may in each case be substituted, and where R5 and R6 may be bonded homocyclically or heterocyclically to one another in the form of a ring structure; and where, preferably, R5 and R6 are H and R9 and R10 are H. R3 here is selected from the group consisting of H, alkyl, fluorinated alkyl, partly fluorinated alkyl, alkoxy, amino, aryl, and an electron-withdrawing alkyl group having at least one C—C double bond, wherein H may be substituted by CN or F; preferably, R3 is an electron-withdrawing alkyl group having at least one C—C double bond, and R2 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double bond, wherein H may be substituted by CN or F; preferably R2 is an electron-withdrawing alkyl group having at least one C—C double bond.

In a preferred embodiment of the invention, X and/or Z is O; the structure here is, in particular, a substituted furan ring. Preferably, at least one furan ring in the groups A1, A2, A3, A4 or A5 on the central indole unit increases the absorption by the compound.

In a preferred embodiment of the invention, the groups A5 and at least one of the groups A1, A2, A3 and A4 are identical.

In a preferred embodiment of the invention, R4 is H, methyl, propyl or isopropyl, where X and Z are O, R4 is H, and R5 and R6 are H.

In a preferred embodiment of the invention, R2 in the group Ib is an electron-withdrawing alkyl group having at least one C—C double bond, wherein H may be substituted by CN or F, and/or R3 in the group Ia is an electron-withdrawing alkyl group having at least one C—C double bond, wherein H may be substituted by CN or F.

In a preferred embodiment of the invention, R2 and/or R3 have at least two C—C double bonds.

In one development of the invention, R2 and R3 are each independently

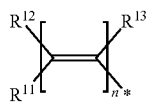

where n is 1, 2, 3 or 4, where * denotes the attachment to the group of the general formula Ia and/or Ib;
R11, R12 and R13 are each independently selected from the group consisting of H, halogen, CN, COO-alkyl, alkenyl, alkynyl, alkoxy, cyclic or open-chain alkyl, cyclic or open-chain alkenyl, where H in each case may be substituted by halogen or CN, with the condition that R11 and R12 are not both H, where R11 and R12 are preferably CN. This realizes the advantageous effects of the present invention in an exceptional manner.

In a preferred embodiment of the invention, R2 and/or R3 is in each case independently

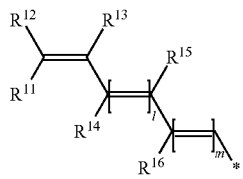

where m is 0, 1 or 2 and l is 0, 1 or 2;
R11, R12, R13, R14, R15 and R16 are each independently selected from the group consisting of H, halogen, CN, COO-alkyl, alkenyl, alkynyl, alkoxy, cyclic or open-chain alkyl, cyclic or open-chain alkenyl, where H in each case may be substituted by halogen or CN, with the condition that R11 and R12 are not both H, where R11 and R12 are preferably CN. A large number of CN groups can achieve particular good acceptor action of the R2 and/or R3 groups.

In a further development of the invention, R2 and R3 are each independently selected from the group consisting of:

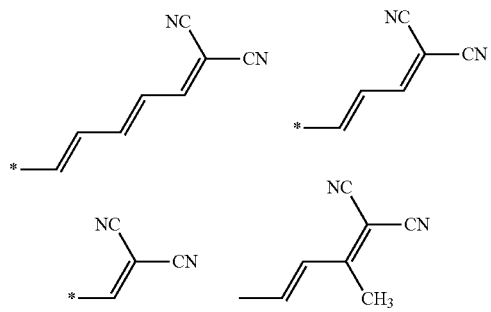

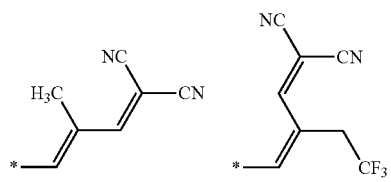

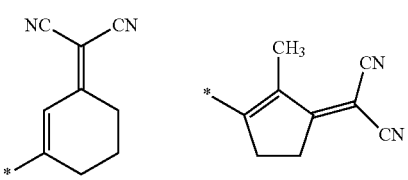

where * denotes the attachment to the group of the general formula Ia and/or Ib, where R2 and R3 are preferably the same.

In one development of the invention, the compound is selected from the group consisting of:

F1

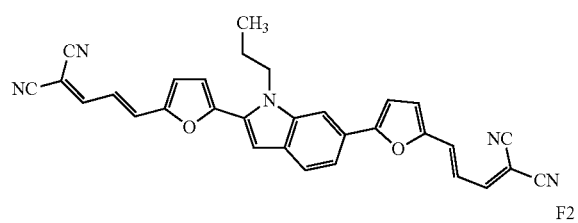

F2

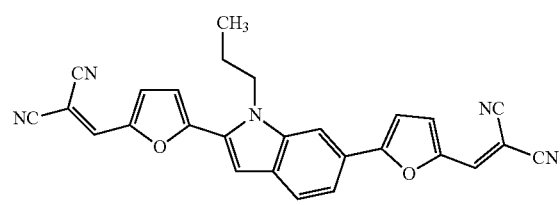

F3

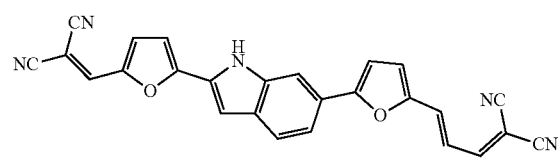

F4

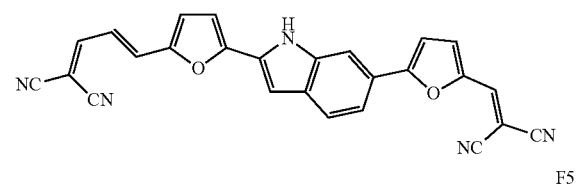

F5

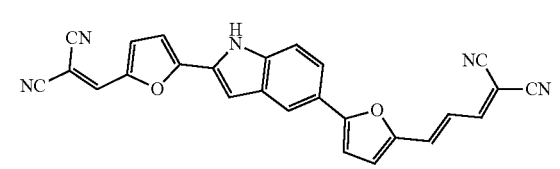

-continued

F6
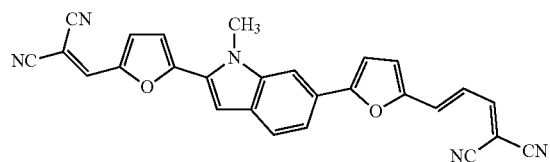

F8
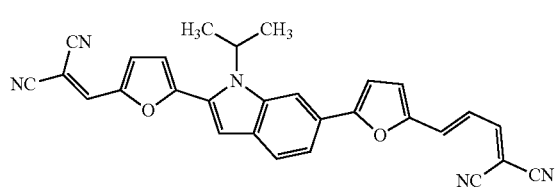

F9
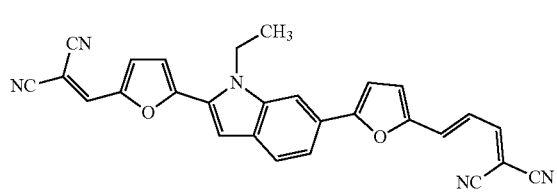

F10
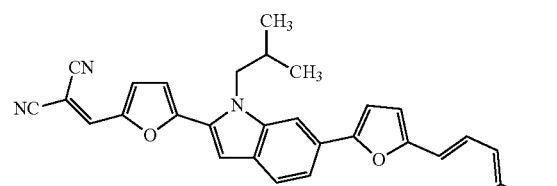

F11
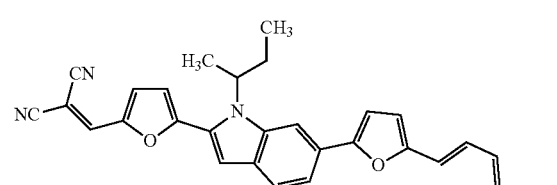

F12
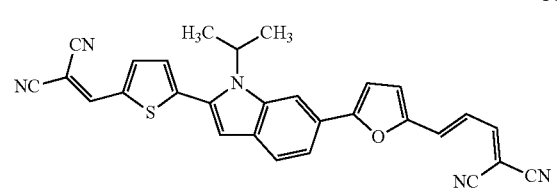

-continued

F15
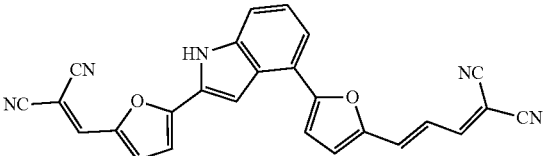

F17
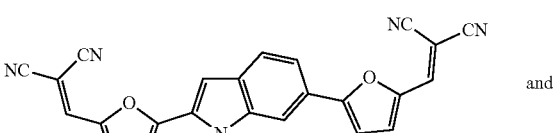
and

F18
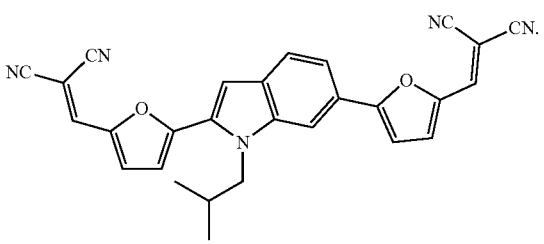

In one development of the invention, the compound is F7 and/or F16

F7
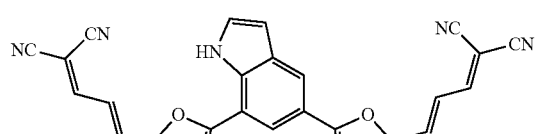

F16
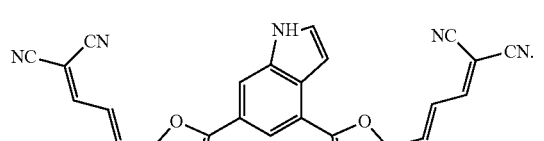

F13
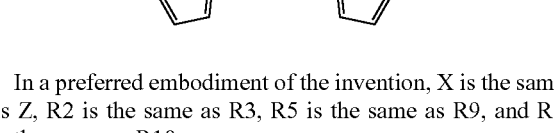

In a preferred embodiment of the invention, X is the same as Z, R2 is the same as R3, R5 is the same as R9, and R6 is the same as R10.

In a preferred embodiment of the invention, the compound of the general formula I additionally has a five- or six-membered ring formed by R5 and R6 and/or R9 and R10; this five-membered ring or six-membered ring may be substituted at further positions.

Organic single or tandem cells are known from the prior art. Published specification DE102004014046A1 discloses a photoactive component, especially a solar cell, consisting of organic layers of one or more pi, ni, and/or pin diodes stacked on top of one another. International patent application WO201116108A1 discloses a photoactive component having an electrode and a counterelectrode, with at least one organic layer system disposed between the electrodes, having at least two photoactive layer systems and, between the photoactive layer systems, at least two different transport layer systems of the same charge carrier type, characterized in that one transport layer system is matched to the energy of one of the two photoactive layer systems and the other transport layer system is transparent.

The object of the present invention is also achieved by providing an optoelectronic component comprising at least one compound of the invention, especially one according to one of the exemplary embodiments described above. For the optoelectronic component, this gives rise in particular to the advantages already elucidated in connection with the compound of the invention. The optoelectronic component comprises a first electrode, a second electrode, and a layer system, the layer system being arranged between the first electrode and the second electrode, characterized in that at least one layer of the layer system comprises at least one compound of the invention.

The efficiency of an organic optoelectronic component depends upon factors including the absorption characteristics of the compound, i.e. the absorber material. Advantageous properties here are especially high absorption and absorption in a broad region of the available spectrum of electromagnetic radiation, since this allows photons of different wavelengths to be utilized for the generation of electrical power.

An optoelectronic component, especially an organic optoelectronic component, is understood to mean, in particular, a component that comprises organic conductive or semiconductive materials, especially a transistor, a light-emitting organic component, an organic photoactive device, a photodetector, or an organic solar cell. Solar cells comprising at least one compound of the invention allow particularly efficient utilization of the short-wave spectrum of visible light.

An organic photovoltaic element (OPV) is understood to mean, in particular, a photovoltaic element having at least one organic photoactive layer, with the organic photoactive layer comprising at least one compound of the invention. A photoactive organic optoelectronic component allows electromagnetic radiation, for instance in the visible light wavelength range, to be converted into electrical current by making use of the photoelectric effect. The conversion requires organic semiconductor materials that show sufficiently good absorption properties.

In a preferred embodiment of the invention, the optoelectronic component is a solar cell, an FET, an LED or a photodetector, preferably an organic solar cell (OPV), an OFET, an OLED or an organic photodetector.

The organic electronic component here especially comprises an electrode and a counterelectrode, with an organic photoactive layer disposed between the electrodes. This organic photoactive layer has a function that is important for the optoelectronic component, in particular a charge-carrier transport function such as the transport of holes (p-conducting) or the transport of electrons (n-conducting). The organic photoactive layer is in particular a photoactive layer in which excitons (electron-hole pairs) are formed by radiation from visible light, UV radiation, and/or IR radiation. The organic materials are printed, glued, coated, vapor-deposited or otherwise applied onto the foils in the form of thin films or small volumes. All processes that are also used for electronics on glass, ceramic or semiconducting substrates can likewise be used for producing the thin layers.

In one development of the invention, the layer system has at least one photoactive layer, preferably an absorber layer, wherein the at least one photoactive layer comprises the at least one compound of the invention. In a preferred embodiment of the invention, the photoactive layer is disposed between the first electrode and the second electrode.

In one development of the invention, the layer system has at least two photoactive layers, preferably at least three photoactive layers, or preferably at least four photoactive layers, preferably absorber layers.

In a preferred embodiment of the invention, the organic solar cell has a photoactive layer that comprises at least one organic donor material in contact with at least one organic acceptor material, the donor material and the acceptor material forming a donor-acceptor heterojunction, specifically also what is called a bulk heterojunction (BHJ), and wherein the photoactive layer comprises at least one compound of the invention.

In a preferred embodiment of the invention, the optoelectronic component comprises at least one further layer, preferably at least one charge transport layer, especially an electron transport layer and/or a hole transport layer.

In a preferred embodiment of the invention, the at least one charge transport layer, especially at least one electron transport layer and/or at least one hole transport layer, comprises the at least one compound of the invention.

In a preferred embodiment of the invention, the organic solar cell is a single cell, or a tandem, triple, quadruple or other multiple cell.

A tandem cell is understood to mean, in particular, that two functional cells are spatially stacked on top of one another and connected in series, preferably between a first electrode and a second electrode, wherein one or more interlayers may be disposed between the cells. A multiple cell or multijunction cell is accordingly understood to mean that more than two functional cells are stacked one on top of another in space and connected in series, where an interlayer may be arranged between the cells.

In a preferred embodiment of the invention, the optoelectronic component comprises a substrate, with the layer system disposed on the substrate between the first electrode and the second electrode; in particular, it is possible for one of the electrodes of the optoelectronic component to have been applied directly to the substrate.

In one development of the invention, the photoactive layer takes the form of a mixed layer of the at least one compound of the invention and at least one further compound, or of a mixed layer of the at least one compound of the invention and at least two further compounds, the compounds preferably being absorber materials.

In a preferred embodiment of the invention, the optoelectronic component takes the form of a nip, ni, ip, pnip, pni, pip, nipn, nin, ipn, pnipn, or pipn cell, or of a combination of nip, ni, ip, pnip, pni, pip, nipn, nin, ipn, pnipn, or pipn cells that contain at least one i layer.

An i layer is understood to mean, in particular, an intrinsic undoped layer. One or more i layers may consist here of one material (planar heterojunctions, PHJ) or else of a mixture of two or more materials, called bulk heterojunctions (BHJs) having an interpenetrating network.

In a preferred embodiment, the compound of the invention and/or a layer comprising the at least one compound of the invention can be deposited by means of vacuum processing, gas-phase deposition or solvent processing, particularly preferably by means of vacuum processing.

The object of the present invention is also achieved by providing for the use of a compound of the invention in an optoelectronic component, preferably in an organic optoelectronic component, in particular according to one of the working examples described above. The use of the compound of the invention in an optoelectronic component gives rise in particular to the advantages that have already been elucidated in connection with the compound of the invention and with the optoelectronic component comprising the at least one compound of the invention.

In a preferred embodiment of the invention, the optoelectronic component, preferably the organic optoelectronic component, is an organic solar cell.

In the following some specific working examples of the compound of the invention and the optical properties thereof are demonstrated. Table 1 shows an overview of the melting points and absorption maxima (in nm and eV in the solvent (LM)) of these compounds of the invention. The associated absorption spectra of the compounds listed in table 1 are shown in FIGS. 3 to 15. The spectral data relate to vacuum vapor-deposition layers on quartz glass having a thickness of 30 nm.

TABLE 1

| No. | Structure | m.p./ °C.[a] | λmax (film)/ nm[b] | λmax (film)/eV[b] (FWHM/nm) |
|---|---|---|---|---|
| F1 | [chemical structure] | 300 | 589 | 2.10 (385) |
| F2 | [chemical structure] | 263 | 583 | 2.13 (169) |
| F3 | [chemical structure] | 297 | 570 | 2.18 (238) |
| F4 | [chemical structure] | 295 | 608 | 2.04 (277) |
| F5 | [chemical structure] | 285 | 535 | 2.32 (191) |
| F6 | [chemical structure] | 312 | 570 | 2.18 (265) |

TABLE 1-continued

| No. | Structure | m.p./ °C.[a] | λmax (film)/ nm[b] | λmax (film)/eV[b] (FWHM/nm) |
|---|---|---|---|---|
| F7 | 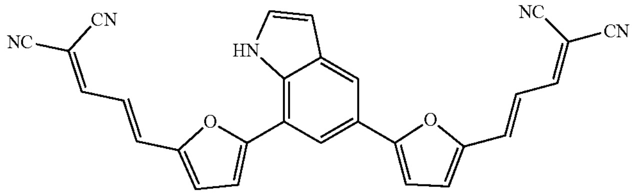 [SMILES: N#CC(C#N)=C/C=C/c1ccc(-c2cc(-c3ccc(/C=C/C=C(C#N)C#N)o3)c3[nH]ccc3c2)o1] | 308 | 533 | 2.33 (212) |
| F8 | 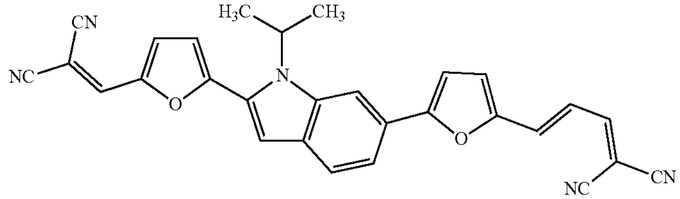 [SMILES: CC(C)n1c(-c2ccc(C=C(C#N)C#N)o2)cc2ccc(-c3ccc(/C=C/C=C(C#N)C#N)o3)cc21] | 312 | 569 | 2.18 (259) |
| F9 | 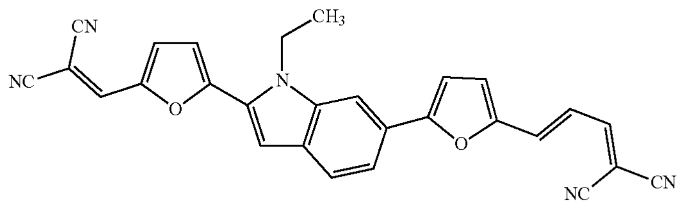 [SMILES: CCn1c(-c2ccc(C=C(C#N)C#N)o2)cc2ccc(-c3ccc(/C=C/C=C(C#N)C#N)o3)cc21] | 295 | 577 | 2.15 (251) |
| F10 | 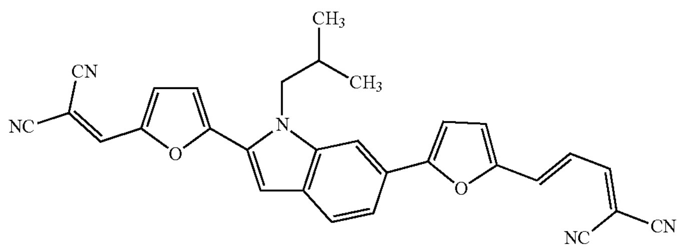 [SMILES: CC(C)Cn1c(-c2ccc(C=C(C#N)C#N)o2)cc2ccc(-c3ccc(/C=C/C=C(C#N)C#N)o3)cc21] | 235 | 577 | 2.15 (162) |
| F11 | 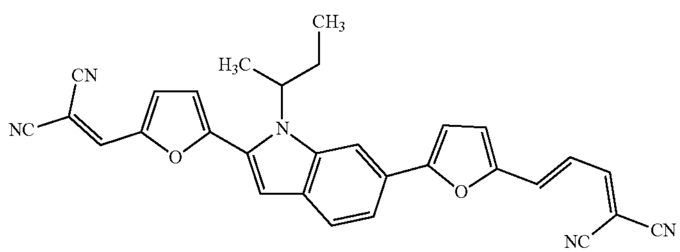 [SMILES: CCC(C)n1c(-c2ccc(C=C(C#N)C#N)o2)cc2ccc(-c3ccc(/C=C/C=C(C#N)C#N)o3)cc21] | 269 | 569 | 2.18 (236) |
| F12 | 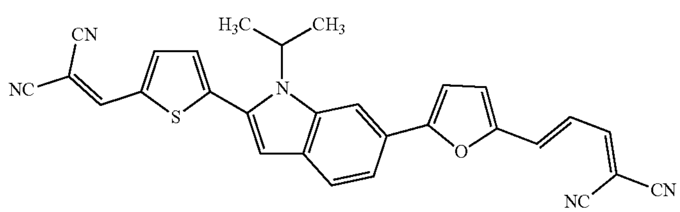 [SMILES: CC(C)n1c(-c2ccc(C=C(C#N)C#N)s2)cc2ccc(-c3ccc(/C=C/C=C(C#N)C#N)o3)cc21] | 268 | 557 | 2.23 (213) |
| F13 | 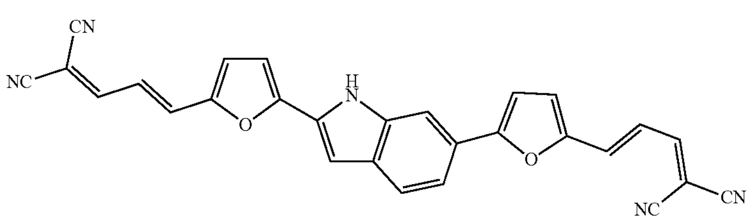 [SMILES: N#CC(C#N)=C/C=C/c1ccc(-c2ccc3cc(-c4ccc(/C=C/C=C(C#N)C#N)o4)[nH]c3c2)o1] | 307 | | |

TABLE 1-continued

| No. | Structure | m.p./ °C.[a] | λmax (film)/ nm[b] | λmax (film)/eV[b] (FWHM/nm) |
|---|---|---|---|---|
| F14 | 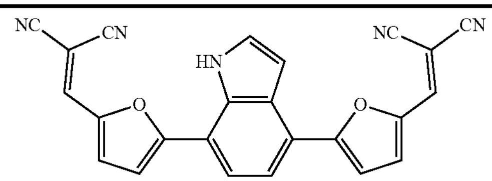 | 369 | | |
| F15 | 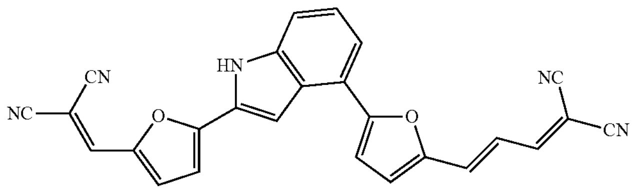 [SMILES: N#CC(C#N)=C/C=C/c1ccc(-c2cccc3[nH]c(-c4ccc(C=C(C#N)C#N)o4)cc23)o1] | 322 | | |
| F16 | 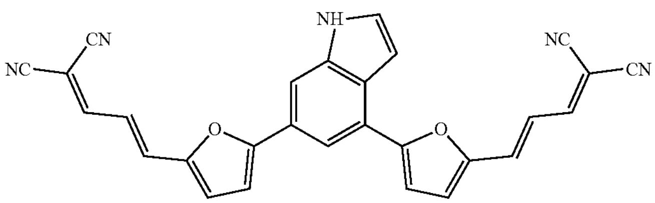 [SMILES: N#CC(C#N)=C/C=C/c1ccc(-c2cc(-c3ccc(/C=C/C=C(C#N)C#N)o3)c3cc[nH]c3c2)o1] | 290 | 538 | 2.21 (218) |
| F17 | 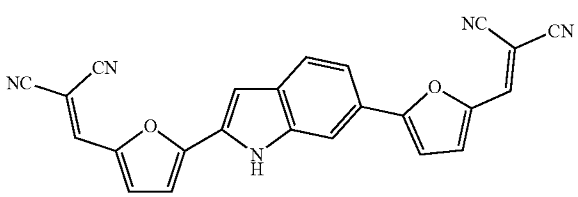 [SMILES: N#CC(C#N)=Cc1ccc(-c2ccc3cc(-c4ccc(C=C(C#N)C#N)o4)[nH]c3c2)o1] | 357 | 577 | 2.15 (175) |
| F18 | 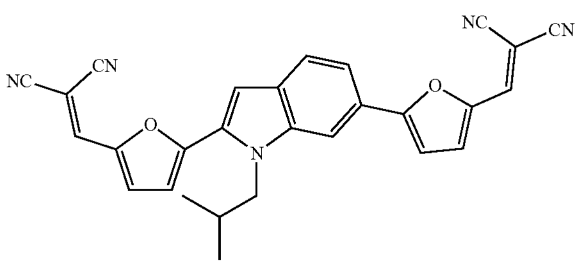 [SMILES: CC(C)Cn1c(-c2ccc(C=C(C#N)C#N)o2)cc2ccc(-c3ccc(C=C(C#N)C#N)o3)cc21] | 276 | 574 | 2.16 (221) |

[a]onset DSC (dynamic differential calorimetry)
[b]in dichloromethane

The optical properties were determined experimentally. The absorption maxima λmax were determined with a dilute solution in a cuvette in dichloromethane using a photometer. The measured absorption maxima of all compounds described are between 530 and 610 nm.

The compounds of the invention are notable for particularly high absorption within a broad spectrum of visible light. The compounds of the invention thus enable absorption of photons over a comparatively broad spectral region comprising a high proportion of short-wave visible sunlight, and conversion thereof to electrical energy.

It can be inferred from the absorption spectra in table 1 that the compounds of the invention have particularly good absorptivity of radiation and hence have a relatively high integral over the optical density in the visible spectral region. What is meant here by "integral" is the area beneath a curve in the absorption spectrum, which is an important feature for the suitability of the material as photoactive material.

Table 2 shows various parameters of compounds of the invention in direct comparison. The photovoltaic parameters of open-circuit voltage Uoc, short-circuit current Jsc, and fill factor FF relate in each case to the same structure of a solar cell.

For examination of the compounds of the invention, i.e. the use thereof as absorber materials in organic optoelectronic components, the current-voltage curve was measured in a BHJ cell having the structure: glass with ITO/C60 (15 nm)/compound of the invention (absorber material):C60 (30 nm, 3:2, 50° C.)/BPAPF (10 nm)/BPAPF:NDP9 (30 nm, 10% by weight NDP9)/NDP9 (1 nm)/Al (100 nm) under AM1.5 illumination (AM=air mass; AM=1.5, in this spectrum the global radiation power is 1000 W/m²; AM=1.5 as standard value for the measurement of solar modules), the photoactive layer being a bulk heterojunction (BHJ). A transparent cover contact made of ITO (indium tin oxide) is applied to a glass substrate. ITO serves here as the electrode, and the neighboring fullerene C60 as the electron transport layer (ETL), adjoining this is the photoactive C60 layer as electron acceptor material and the respective compound of the invention as hole acceptor material (donor material), followed by BPAPF (9,9-bis[4-(N,N-bis(biphenyl-4-yl)amino)phenyl]-9H-fluorene) as a hole transport layer (HTL) and BPAPF doped with NDP9 (Novaled AG), followed by an electrode made of aluminum (see FIG. 2).

The advantageous synergistic effect of compounds of the invention that have furan groups or thiophene groups in interaction with an indole unit is shown in table 2.

TABLE 2

| Substance | OD integral for 30 nm film (400-900 nm) | Uoc [V] | Jsc/EQE [mA/cm$^2$] | FF [%] | eff [%] |
|---|---|---|---|---|---|
| F1 | 97 | 0.83 | 10.8 | 62.7 | 5.62 |
| F2 | 63 | 1.02 | 8.0 | 61.7 | 5.03 |
| F3 | 95 | 0.98 | 11.5 | 73.8 | 8.32 |
| F4 | 97 | 0.94 | 11.9 | 72.1 | 8.07 |
| F5 | 103 | 1.01 | 7.7 | 62.3 | 4.85 |
| F6 | 83 | 0.96 | 13.8 | 72.5 | 9.60 |
| F7 | 84 | 1.0 | 9.8 | 63.2 | 6.23 |
| F8 | 86 | 0.98 | 12.8 | 67.9 | 8.52 |
| F9 | 90 | 0.98 | 13.6 | 70.3 | 9.37 |
| F10 | 85 | 1.01 | 11.8 | 56.5 | 6.73 |
| F11 | 76 | 0.98 | 11.3 | 56.7 | 6.28 |
| F12 | 77 | 1.03 | 8.9 | 50.7 | 4.65 |
| F13 | | 0.87 | 12.2 | 70.3 | 7.46 |

The particularly advantageous properties of the compounds of the invention are also demonstrated, in an identical solar cell structure, in the photovoltaic parameters of open-circuit voltage Uoc, short-circuit current Jsc, and fill factor FF. An elevated fill factor FF suggests that the compounds of the invention have not just improved absorption properties but also superior charge carrier transport properties. Depending on the charge transport properties and the absorption properties, it is possible to achieve high photocurrents with good fill factors. It is thus possible to produce very well-combined tandem/triple/quadruple or multijunction solar cells. Of the compounds shown in table 2, compounds F3, F4, F6, F8, F9 and F13 have the best optical properties; more particularly, the highest cell efficiency (eff), i.e. the highest efficiency, of an organic solar cell produced therewith was achieved for these compounds, and among these compounds F6 and F9 have the highest efficiency in the solar cells. These compounds each have a furan ring and/or thiophene ring, especially one furan ring each, on the five-membered ring and on the six-membered ring of the central indole unit. Additionally advantageous is an H, or a methyl, ethyl, propyl or butyl group, especially an isopropyl, isobutyl or s-butyl group, on the N of the pyrrole ring of the central indole unit. Preferably, further five-membered rings (Ia, IIa) are attached in the 2' and 6' positions of the central indole unit. The two outer five-membered rings (Ia, IIa) preferably each have a dicyanovinyl and/or a butadienyldicyano group.

FIG. 1 shows a working example of a synthesis scheme for synthesis of compounds of the invention.

The general preparation of the compound of the invention is known to those skilled in the art from the prior art. Reference in this context is made in particular to international applications WO2017114937A1 and WO2017114938A1.

FIG. 1 shows general syntheses of compounds of the invention. In this way, compounds F2, F3, F4, F5, F6, F8, F9, F10, F11, F12, F14, F15, F17 and F18 are obtainable in a simple manner and in good yields. Compounds F1, F7, F13 and F16 are prepared by a synthesis disclosed in international applications WO2017114937A1 and WO2017114938A1. The positions of linkage of substituents (Ia, IIa) to the central indole unit are summarized in table 3.

TABLE 3

| Compound No. | n | m | Position of linkage to indole |
|---|---|---|---|
| F1 | 1 | 1 | 2.6 |
| F2 | 0 | 0 | 2.6 |
| F3 | 0 | 1 | 2.6 |
| F4 | 1 | 0 | 2.6 |
| F5 | 0 | 1 | 2.5 |
| F6 | 0 | 1 | 2.6 |
| F7 | 1 | 1 | 5.7 |
| F8 | 0 | 1 | 2.6 |
| F9 | 0 | 1 | 2.6 |
| F10 | 0 | 1 | 2.6 |
| F11 | 0 | 1 | 2.6 |
| F12 | 0 | 1 | 2.6 |
| F13 | 1 | 1 | 2.6 |
| F14 | 0 | 0 | 4.7 |
| F15 | 0 | 1 | 2.4 |
| F16 | 1 | 1 | 4.6 |
| F17 | 0 | 0 | 2.6 |
| F18 | 0 | 0 | 2.6 |

The inventive compound of the general formula I

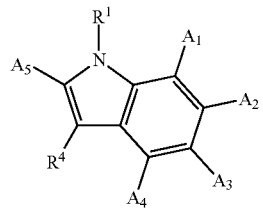

is characterized in that R1 is selected from the group consisting of H, alkoxy, alkyl, fluorinated alkyl, partly fluorinated alkyl, and aryl; R4 is selected from the group consisting of H, halogen, CN, alkoxy, alkyl, fluorinated alkyl, partly fluorinated alkyl, branched or linear, cyclic or open-chain alkyl, amino, aryl, and alkenyl; at least one A1, A2, A3 or A4 in each case is independently the group Ia

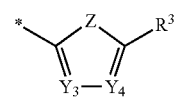

where, in each case, * denotes the attachment to the compound of the general formula I; Z is selected from the group consisting of O, S, Se, and N—R8, where R8 is selected from the group consisting of H, alkoxy, alkyl, fluorinated alkyl, partly fluorinated alkyl, and aryl;

Y3 is N or C—R9 where R9 is selected from the group consisting of H, halogen, alkoxy, branched or linear, cyclic or open-chain alkyl, alkenyl, and aryl, wherein H may in each case be substituted;

Y4 is N or C—R10 where R10 is selected from the group consisting of H, halogen, alkoxy, branched or linear, cyclic or open-chain alkyl, alkenyl, and aryl, wherein H may in each case be substituted; where R9 and R10 may be bonded homocyclically or heterocyclically to one another in the form of a ring structure; and R3 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double bond, wherein H may be substituted by CN or F; the other A1, A2, A3 or A4 are each independently selected from the group consisting of H, halogen, CN, alkoxy, alkyl, fluorinated alkyl, partly fluorinated alkyl, and amino; and A5 is selected from the group consisting of H, alkyl, alkoxy and the group Ib

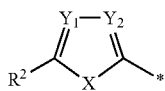

where * denotes the attachment to the compound of the general formula I; X is selected from the group consisting of O, S, Se, and N—R7, where R7 is selected from the group consisting of H, alkoxy, alkyl, fluorinated alkyl, partly fluorinated alkyl, and aryl; Y1 is N or C—R5 where R5 is selected from the group consisting of H, halogen, alkoxy, branched or linear, cyclic or open-chain alkyl, alkenyl, and aryl, wherein H may in each case be substituted; Y2 is N or C—R6 where R6 is selected from the group consisting of H, halogen, alkoxy, branched or linear, cyclic or open-chain alkyl, alkenyl, and aryl, wherein H may in each case be substituted; and where R5 and R6 may be bonded homocyclically or heterocyclically to one another in the form of a ring structure; and R2 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double bond, wherein H may be substituted by CN or F.

In one embodiment of the invention, the compound is a compound of the general formula II

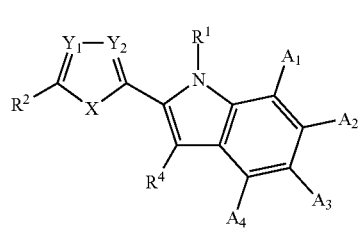

where R1 is preferably selected from the group consisting of H and alkyl; R4 is preferably selected from the group consisting of H, halogen, CN, alkoxy and alkyl; and where X and Z are each independently O or S.

In a further embodiment of the invention, the compound is a compound of the general formula VII

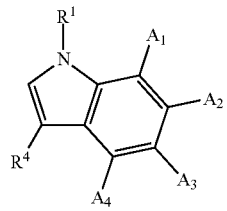

where R1 is preferably selected from the group consisting of H, methyl, ethyl, propyl, isopropyl, butyl, isobutyl and s-butyl; R4 is preferably selected from the group consisting of H, halogen, CN, alkoxy and alkyl; and where Z is O or S.

In a further embodiment of the invention, at least one A1, A2, A3 or A4 is independently a

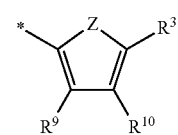

where R3 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double bond, wherein H may be substituted by CN or F; R9 is selected from the group consisting of H, halogen, alkoxy, branched or linear, cyclic or open-chain alkyl, alkenyl, aryl, wherein H may in each case be substituted; R10 is selected from the group consisting of H, halogen, alkoxy, branched or linear, cyclic or open-chain alkyl, alkenyl, and aryl, wherein H may in each case be substituted; and where R9 and R10 may be homocyclically or heterocyclically linked to one another in the form of a ring structure.

In a further embodiment of the invention, the compound is a compound of the general formulae III and/or IV

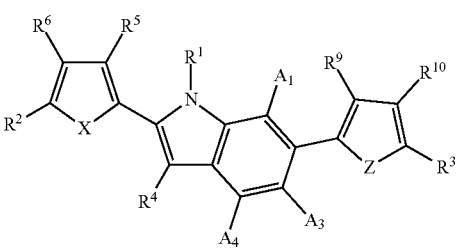

IV

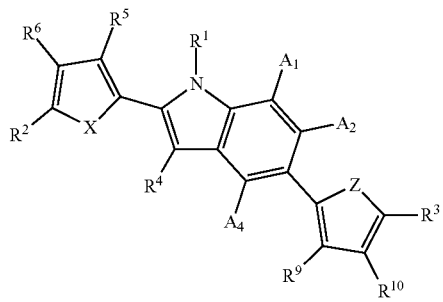

where R1 is selected from the group consisting of H, methyl, ethyl, propyl, isopropyl, butyl, isobutyl and s-butyl; X and Z are each independently O or S; R3 is selected from the group consisting of H, alkyl, fluorinated alkyl, partly fluorinated alkyl, alkoxy, amino, aryl, and an electron-withdrawing alkyl group having at least one C—C double bond, wherein H may be substituted by CN or F;

where, preferably, X and Z are O, R4 is H, and R5 and R6 are H.

In a further embodiment of the invention, in formula III, A1, A3 and A4 are H (formula V), and, in formula IV, A1, A2 and A4 are H (formula VI),

V

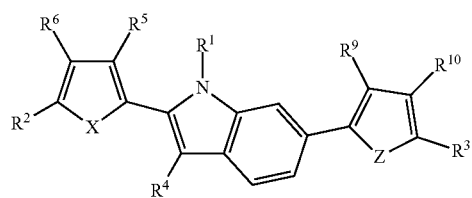

VI

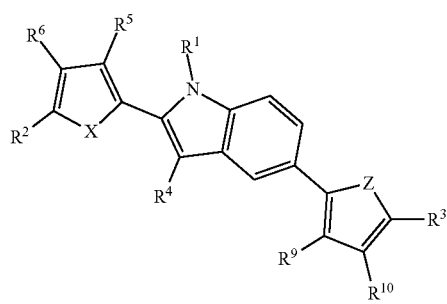

where X and Z are each independently O or S;

where R5 and R6 are preferably H.

In a further embodiment of the invention, the compound is a compound of the general formula VIII and/or IX

VIII

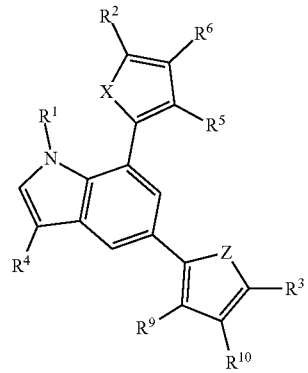

IX

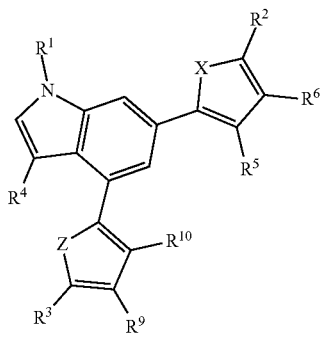

where R1 is H or alkyl; X and Z are each independently O or S; R9 is selected from the group consisting of H, halogen, alkoxy, branched or linear, cyclic or open-chain alkyl, alkenyl, and aryl, wherein H may in each case be substituted; R10 is selected from the group consisting of H, halogen, alkoxy, branched or linear, cyclic or open-chain alkyl, alkenyl, and aryl, wherein H may in each case be substituted; and where R9 and R10 may be bonded homocyclically or heterocyclically to one another in the form of a ring structure; R5 is selected from the group consisting of H, halogen, alkoxy, branched or linear, cyclic or open-chain alkyl, alkenyl, and aryl, wherein H may in each case be substituted; R6 is selected from the group consisting of H, halogen, alkoxy, branched or linear, cyclic or open-chain alkyl, alkenyl, and aryl, wherein H may in each case be substituted; and where R5 and R6 may be bonded homocyclically or heterocyclically to one another in the form of a ring structure;

where, preferably, R5 and R6 are H and R9 and R10 are H.

In a further embodiment of the invention, R2 and R3 are each independently

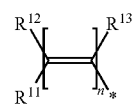

where n is 1, 2, 3 or 4, where * in each case denotes the attachment to the group of the general formula Ia and/or Ib; R11, R12 and R13 are each independently selected from the group consisting of H, halogen, CN, COO-alkyl, alkenyl, alkynyl, alkoxy, cyclic or open-chain alkyl, cyclic or open-chain alkenyl, where H in each case may be substituted by halogen or CN, with the condition that R11 and R12 are not both H, where R11 and R12 are preferably CN.

In a further embodiment of the invention, R2 and R3 are each independently selected from the group consisting of:

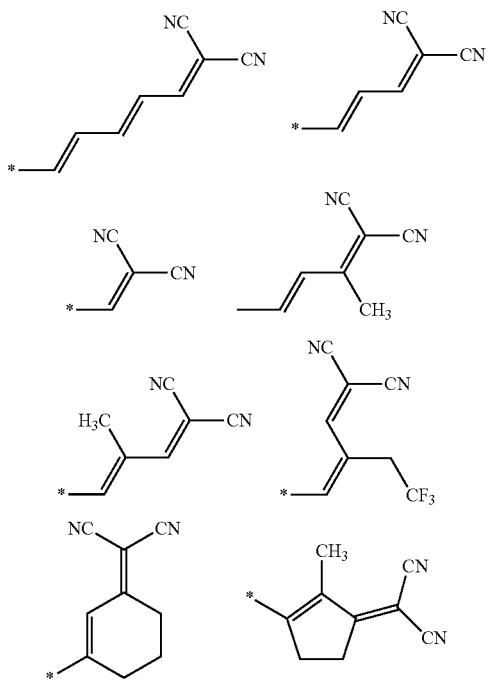

where * denotes the attachment to the group of the general formula Ia and/or Ib, where R2 and R3 are preferably the same.

In a further embodiment of the invention, the compound is selected from the group consisting of:

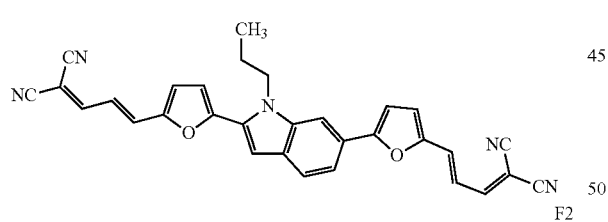

F1

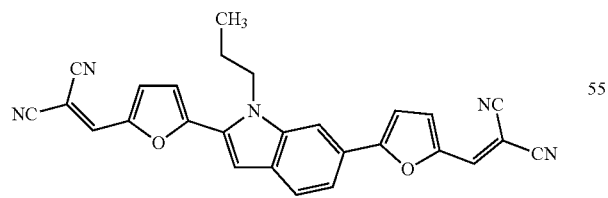

F2

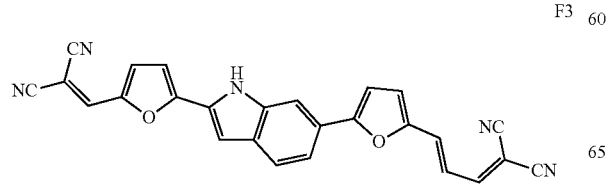

F3

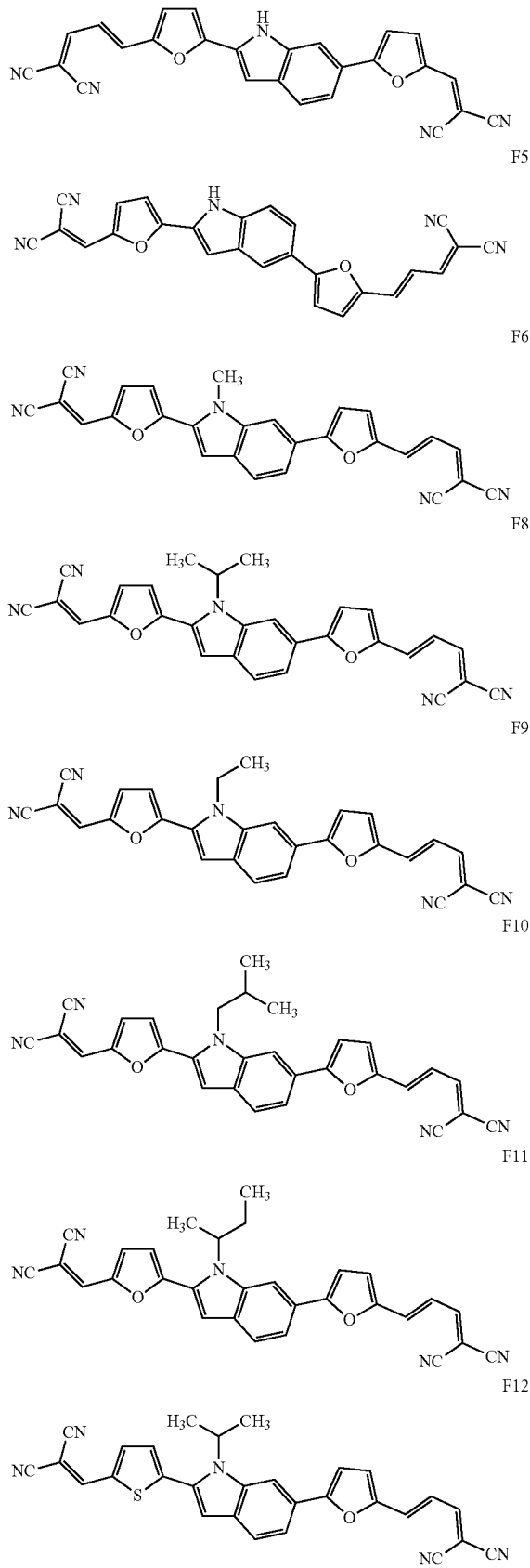

-continued

F13

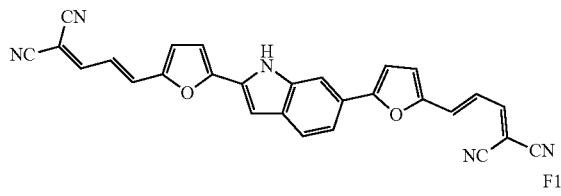

F15

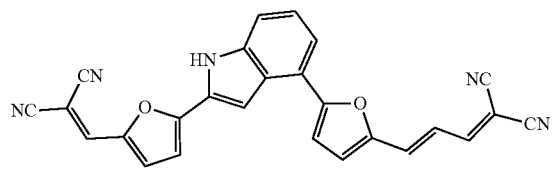

F17

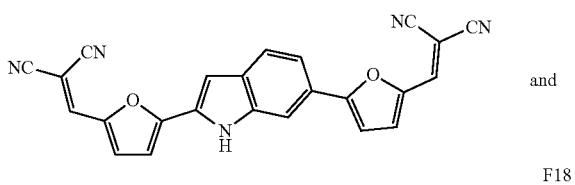

F18

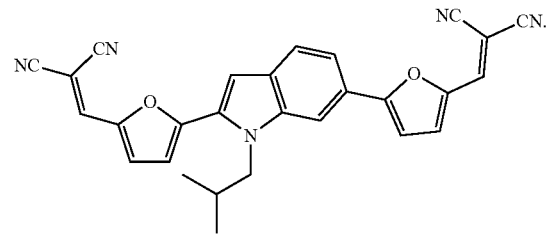

In a further embodiment of the invention, the compound is F7 and/or F16

F7

F16

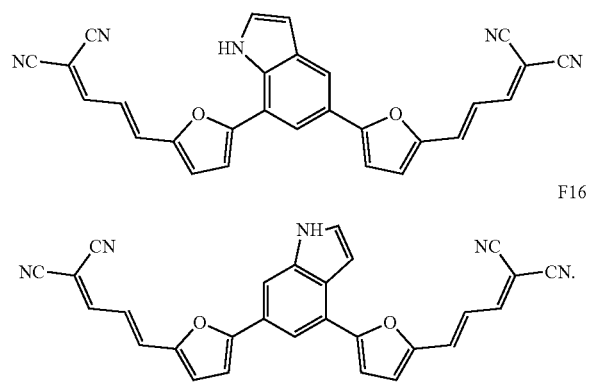

Figure 2:
FIG. 2 a schematic diagram of a working example of an optoelectronic component in cross section.

FIG. 2 shows a schematic diagram of a working example of an optoelectronic component in cross section.

The optoelectronic component comprises a first electrode 1, a second electrode 2, and a layer system 7, the layer system 7 being arranged between the first electrode 1 and the second electrode 2. At least one layer of the layer system 7 comprises at least one compound of the invention.

In one embodiment of the invention, the optoelectronic component is an organic solar cell, an OFET, an OLED or an organic photodetector.

A structure of an organic solar cell known from the prior art consists of a pin or nip diode (Martin Pfeiffer, "Controlled doping of organic vacuum deposited dye layers: basics and applications", Ph.D. thesis TU-Dresden, 1999, and WO2011/161108A1). A pin solar cell consists of a substrate, usually adjoined by a transparent base contact, p layer(s), i layer(s), n layer(s) and a top contact. A nip solar cell consists of a substrate, usually adjoined by a transparent base contact, n layer(s), i layer(s), p layer(s) and a top contact.

In this working example, the optoelectronic component is a solar cell. The solar cell has a substrate 1, for example made of glass, on which there is an electrode 2 comprising ITO, for example. Disposed thereon are an electron transporting layer 3 (ETL) and a photoactive layer 4 comprising at least one compound of the invention, a p-conducting donor material, and an n-conducting acceptor material, e.g. C60 fullerene, either as a planar heterojunction or as a bulk heterojunction. Disposed atop that are a p-doped hole transport layer 5 (HTL), and the electrode 6 made of aluminum.

In a further embodiment of the invention, the layer system 7 has at least one photoactive layer 4, preferably an absorber layer, with the at least one photoactive layer 4 comprising the at least one compound of the invention.

In a further embodiment of the invention, the layer system 7 has at least two photoactive layers, preferably at least three photoactive layers, or preferably at least four photoactive layers.

In a further embodiment of the invention, the photoactive layer takes the form of a mixed layer of the at least one compound of the invention and at least one further compound, or of a mixed layer of the at least one compound of the invention and at least two further compounds, the compounds preferably being absorber materials.

In a further embodiment of the invention, the optoelectronic components have further functional layers, with these especially in the form of a tandem cell, triple cell or multiple cell.

Figure 3A:
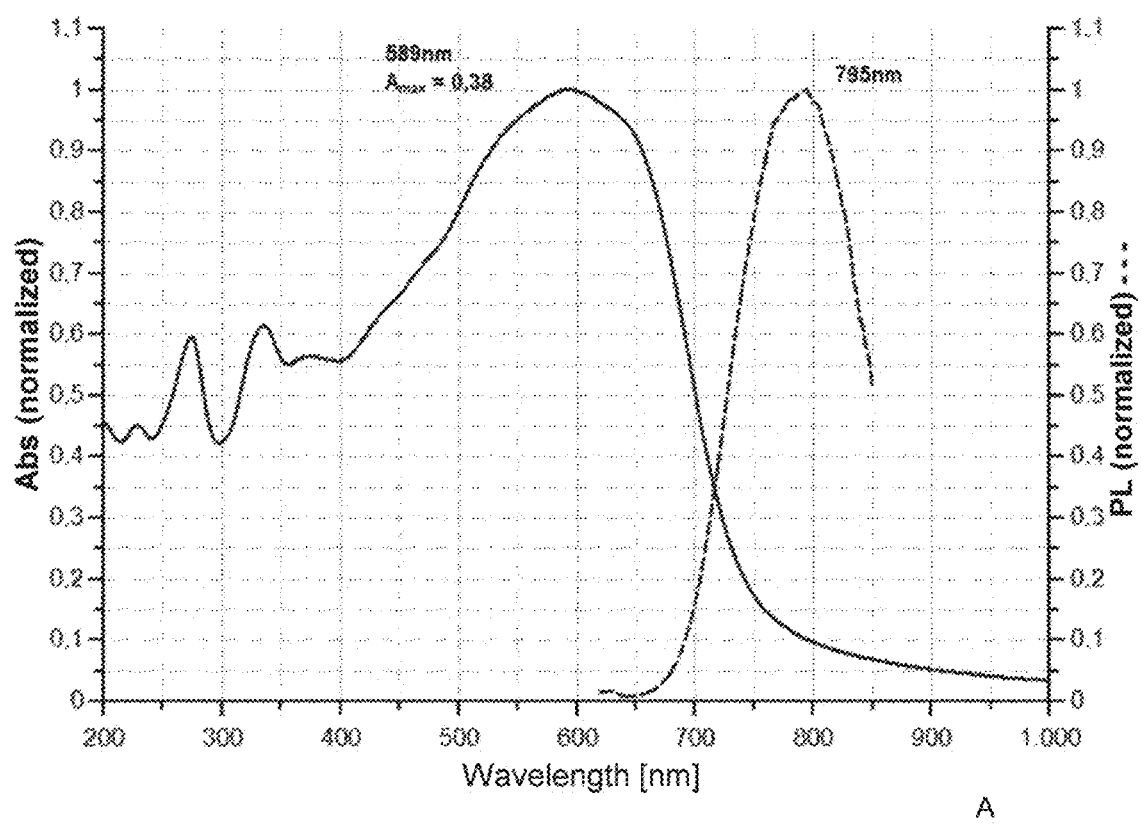
FIG. 3 a graph representation of the absorption spectrum of compound F1, and of the current-voltage curve, of a spectral external quantum yield, and of the fill factor of a BHJ cell comprising compound F1, measured on an organic optoelectronic component in the form of an organic solar cell.
Figure 3B:
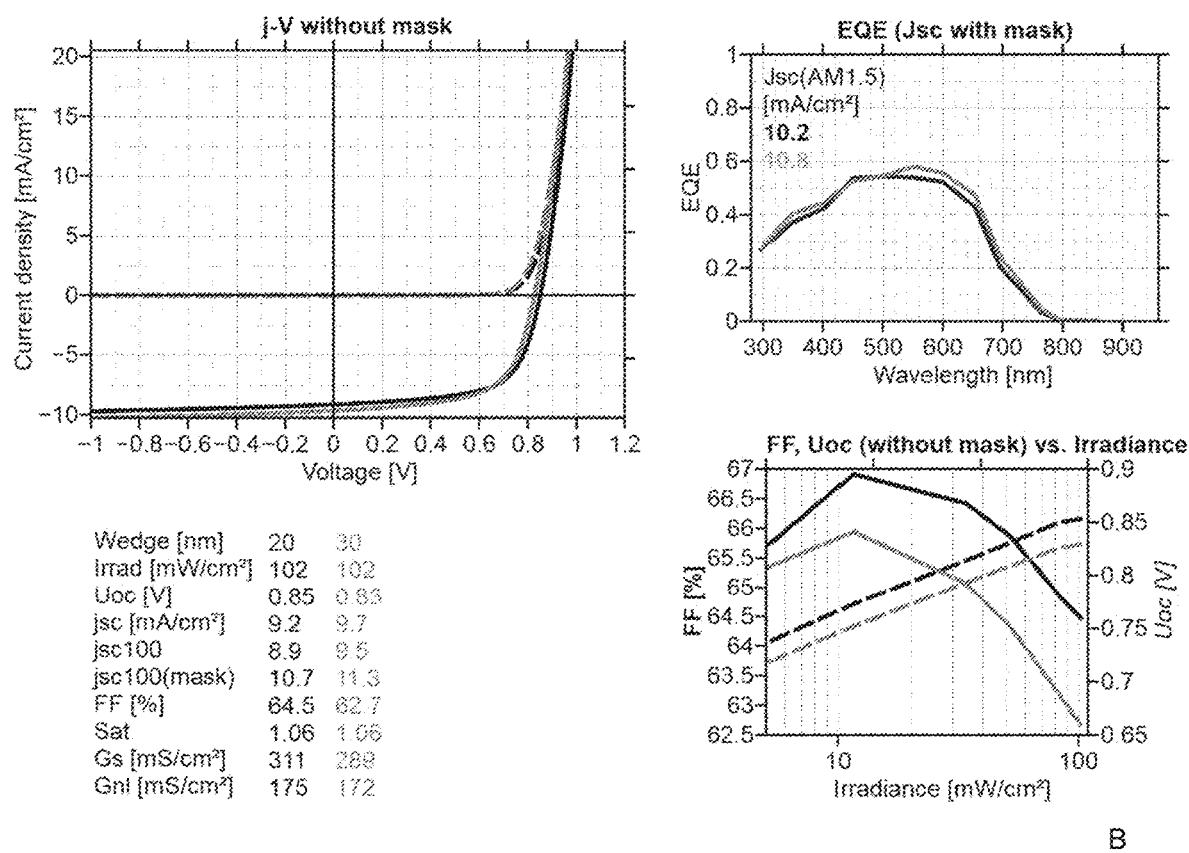

FIGS. 3 to 15 below give specific working examples of the compounds of the invention and the optical properties thereof:

FIG. 3 shows a graph representation of the absorption spectrum of compound F1 (A), and of the current-voltage curve, of a spectral external quantum yield, and of the fill factor of a BHJ cell comprising compound F1, measured on an organic optoelectronic component in the form of an organic solar cell (B).

The absorption spectra (optical density over wavelength in nm) was measured for 30 nm-thick vacuum-deposited layers of the respective compounds F1 to F13 on quartz glass.

The current-voltage curve includes indices that characterize the organic solar cell. The most important indices here are the fill factor FF, the open-circuit voltage Uoc, and the short-circuit current Jsc.

In the specific case, the BHJ cell on the ITO layer has a layer of C60 with a thickness of 15 nm. To this layer was applied compound F1 together with C60 in a thickness of 30 nm. This layer is followed by a layer of BPAPF in a thickness of 10 nm, on top of which is a further layer comprising BPAPF and NDP9 in a thickness of 30 nm. The proportion of BPAPF in this layer is 10 percent by weight based on the entire layer. This layer is adjoined by a further layer comprising NDP9 in a thickness of 1 nm, followed by an aluminum layer in a thickness of 100 nm. The current-voltage curve of a BHJ cell having the structure: ITO/C60 (15 nm)/F1:C60 (30 nm, 3:2, 50° C.)/BPAPF (10 nm)/

BPAPF:NDP9 (30 nm, 10% by weight NDP9)/NDP9 (1 nm)/Al (100 nm) was determined, with the photoactive layer featuring a bulk heterojunction (BHJ). In the optoelectronic component comprising compound F1, the fill factor FF is 62.7%, the open-circuit voltage Uoc is 0.83 V, and the short-circuit current Jsc is 10.8 mA/cm2. The cell efficiency of an optoelectronic component of this type, especially a solar cell, comprising compound F1 is 5.62%.

Compound F1 additionally shows particularly good evaporability at temperatures up to a final temperature of 240° C. to 255° C.

Figure 4A:
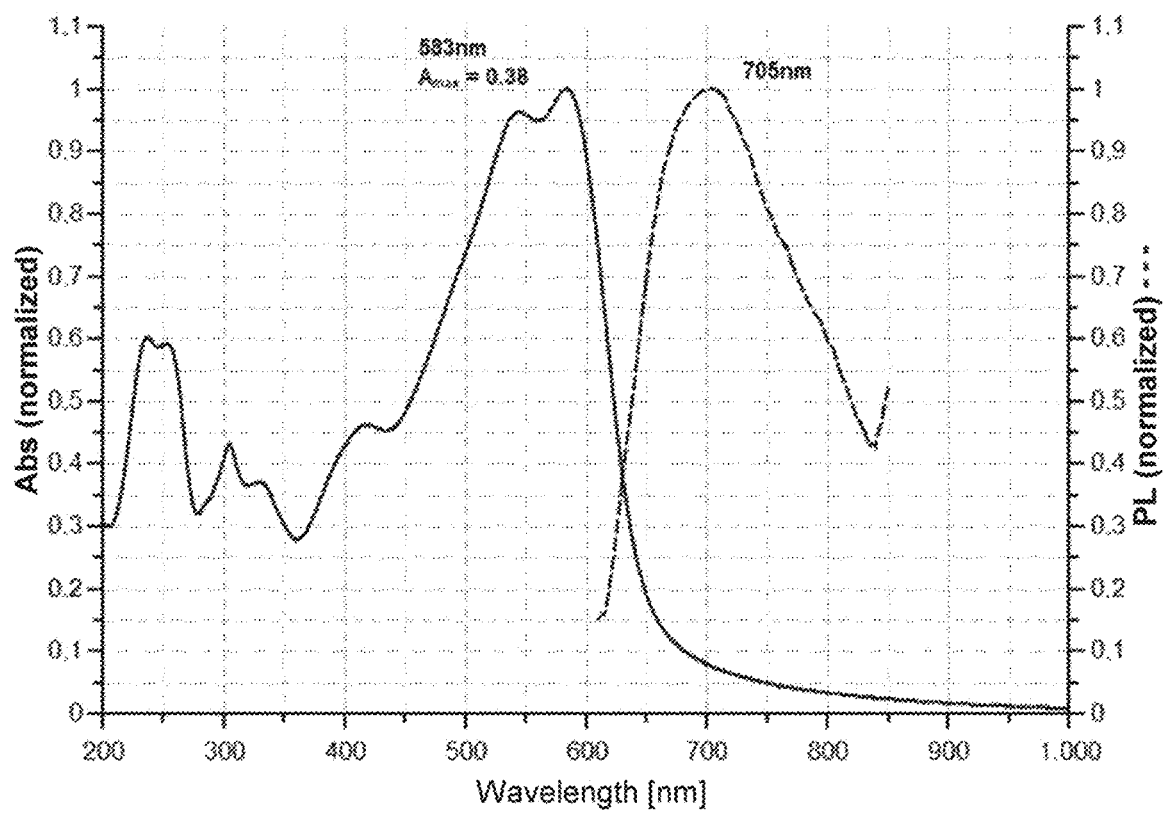
FIG. 4 a graph representation of the absorption spectrum of compound F2, and of the current-voltage curve, of a spectral external quantum yield, and of the fill factor of a BHJ cell comprising compound F2, measured on an organic optoelectronic component in the form of an organic solar cell.
Figure 4B:
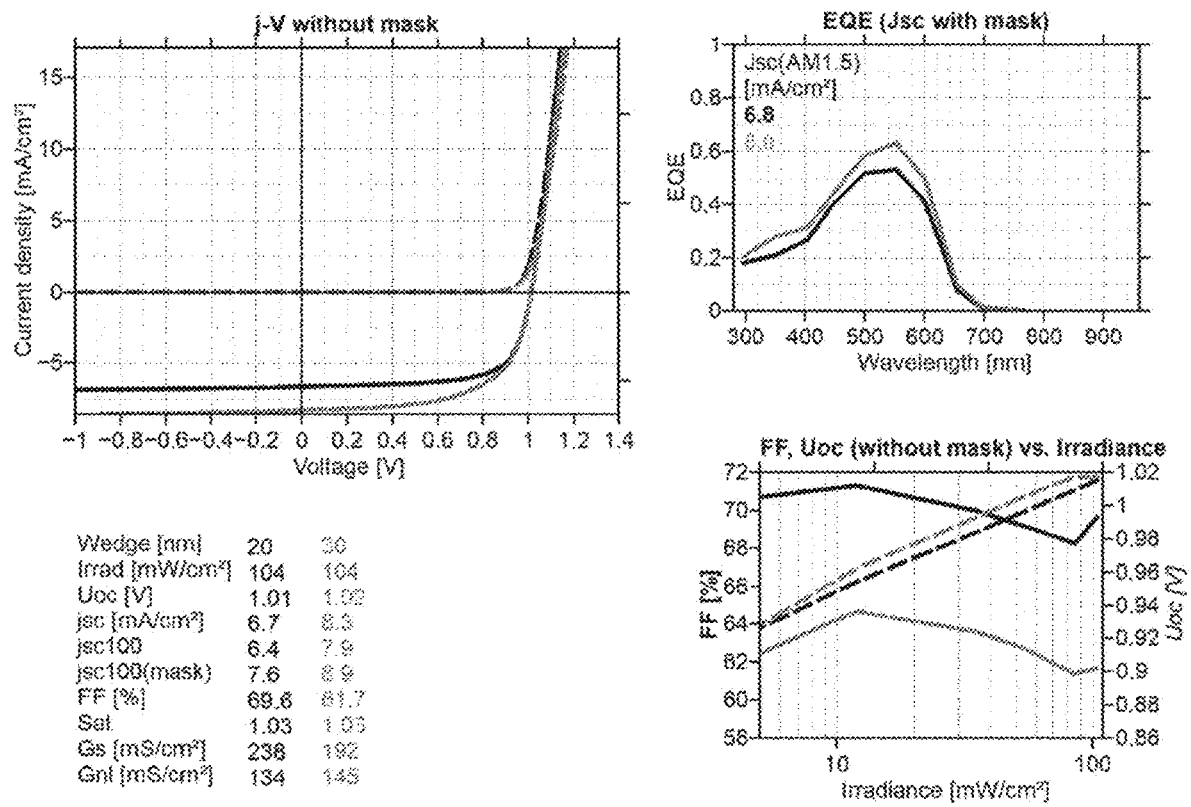

FIG. 4 shows a graph representation of the absorption spectrum of compound F2 (A), and of the current-voltage curve, of a spectral external quantum yield, and of the fill factor of a BHJ cell comprising compound F2, measured on an organic optoelectronic component in the form of an organic solar cell (B).

The current-voltage curve of a BHJ cell having the structure: ITO/C60 (15 nm)/F2:C60 (30 nm, 3:2, 50° C.)/BPAPF (10 nm)/BPAPF:NDP9 (30 nm, 10% by weight NDP9)/NDP9 (1 nm)/Al (100 nm) was determined, with a bulk heterojunction (BHJ) as the photoactive layer. In the optoelectronic component comprising compound F2, the fill factor FF is 61.7%, the open-circuit voltage Uoc is 1.02 V, and the short-circuit current Jsc is 8.0 mA/cm2. The cell efficiency of an optoelectronic component of this type, especially a solar cell, comprising compound F2 is 5.03%.

Figure 5A:
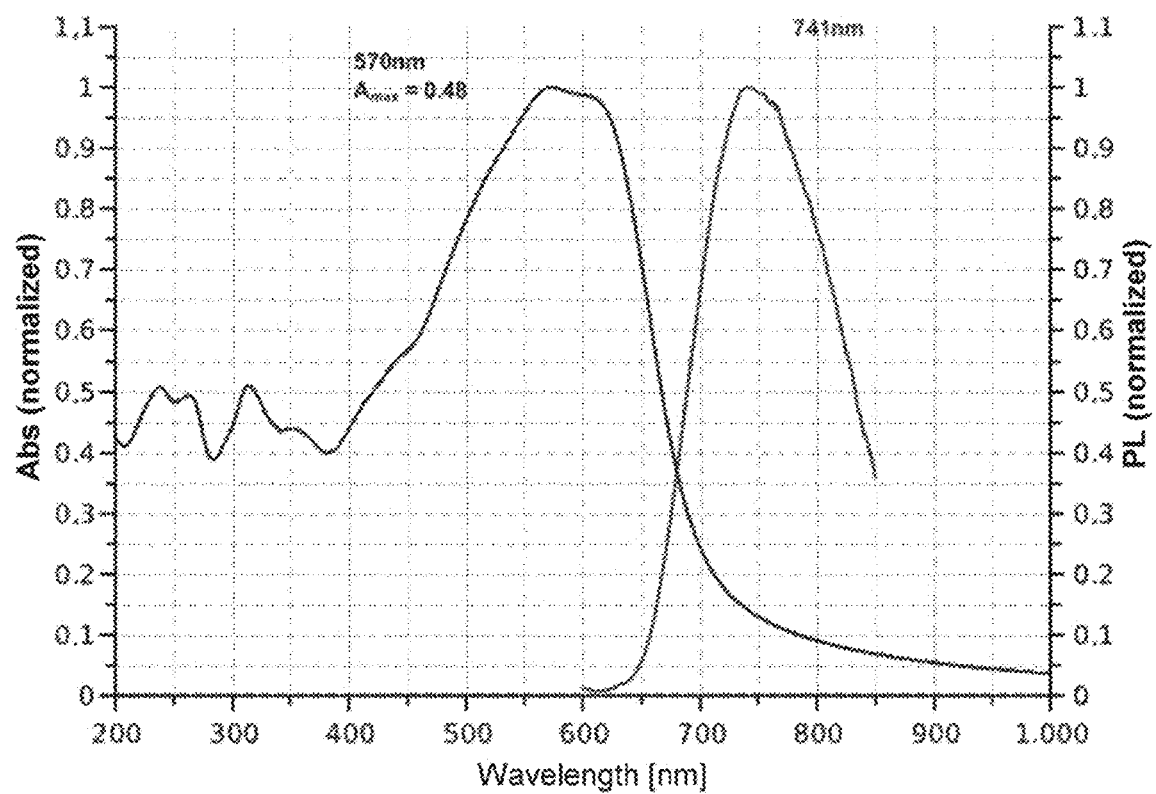
FIG. 5 a graph representation of the absorption spectrum of compound F3, and of the current-voltage curve, of a spectral external quantum yield, and of the fill factor of a BHJ cell comprising compound F3, measured on an organic optoelectronic component in the form of an organic solar cell.
Figure 5B:
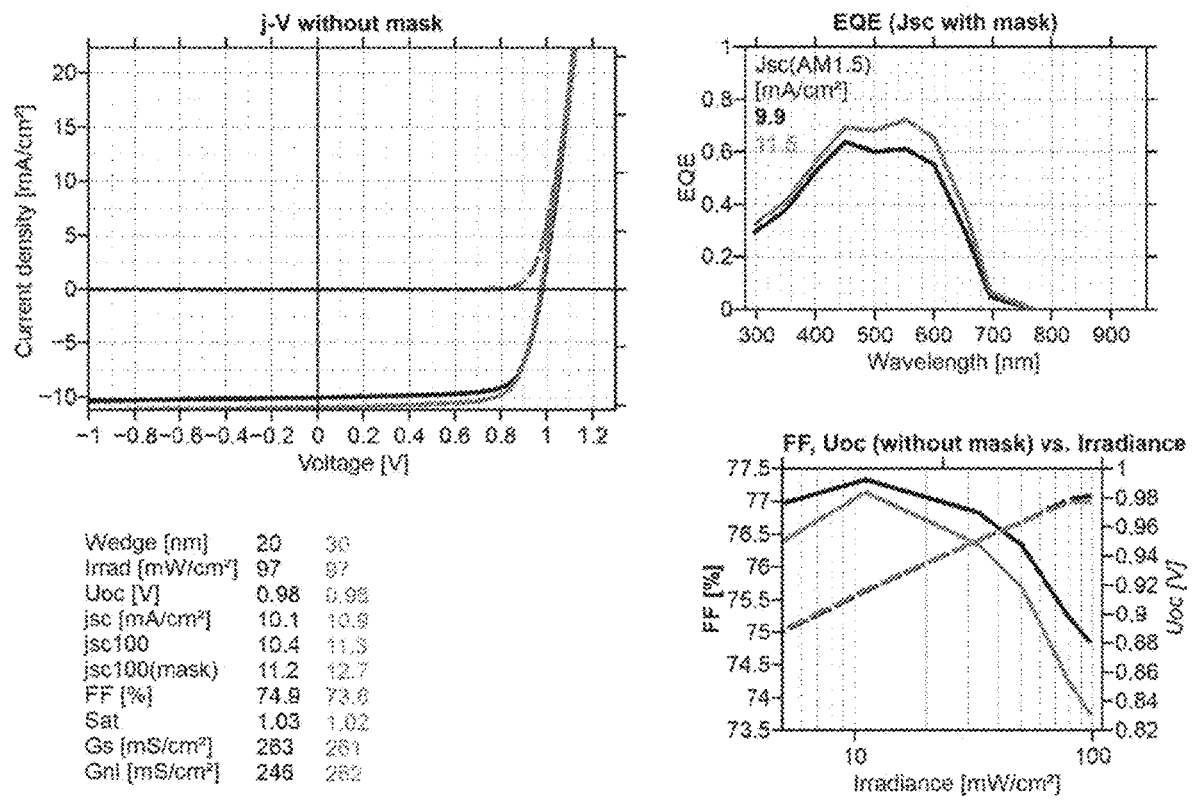

FIG. 5 shows a graph representation of the absorption spectrum of compound F3 (A), and of the current-voltage curve, of a spectral external quantum yield, and of the fill factor of a BHJ cell comprising compound F3, measured on an organic optoelectronic component in the form of an organic solar cell (B).

The current-voltage curve of a BHJ cell having the structure: ITO/C60 (15 nm)/F3:C60 (30 nm, 3:2, 50° C.)/BPAPF (10 nm)/BPAPF:NDP9 (30 nm, 10% by weight NDP9)/NDP9 (1 nm)/Al (100 nm) was determined, with a bulk heterojunction (BHJ) as the photoactive layer. In the optoelectronic component comprising compound F3, the fill factor FF is 73.8%, the open-circuit voltage Uoc is 0.98 V, and the short-circuit current Jsc is 11.5 mA/cm2. The cell efficiency of an optoelectronic component of this type, especially a solar cell, comprising compound F3 is 8.32%. F3 shows particularly good transport properties with a high fill factor FF.

Figure 6A:
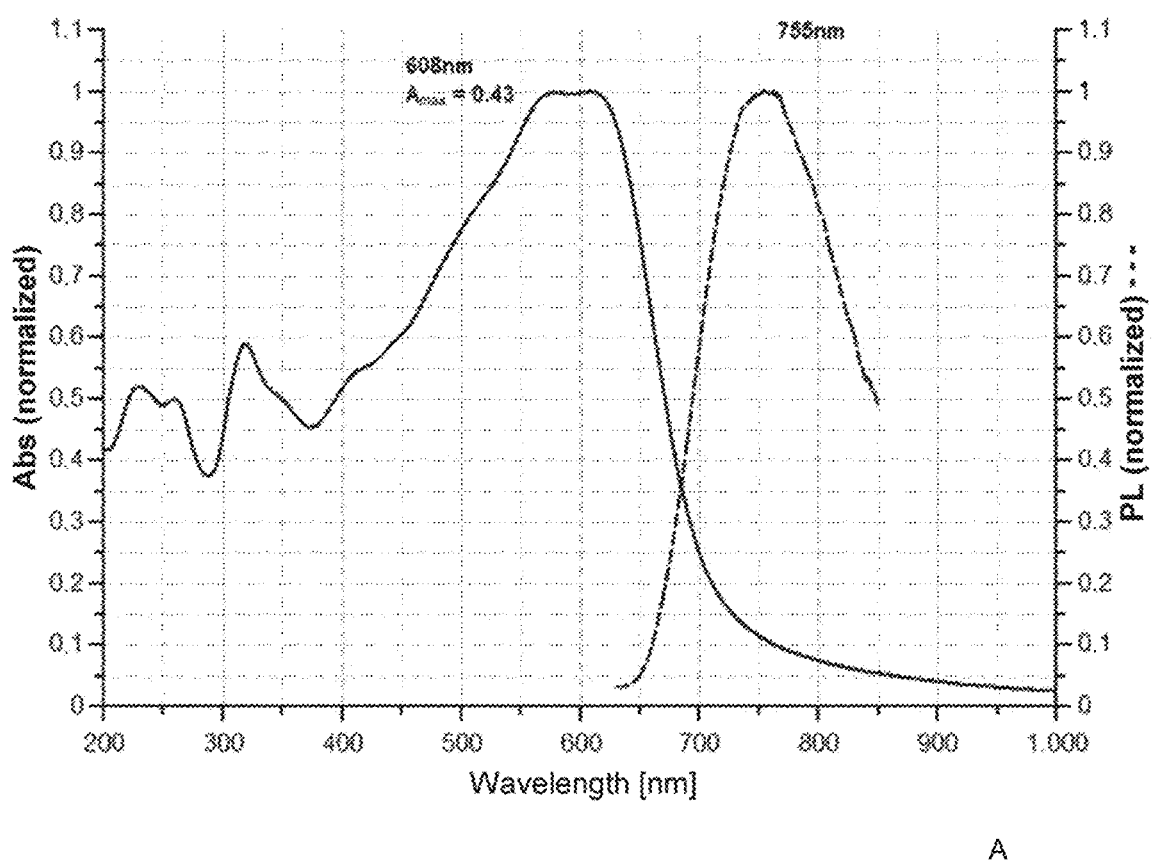
FIG. 6 a graph representation of the absorption spectrum of compound F4, and of the current-voltage curve, of a spectral external quantum yield, and of the fill factor of a BHJ cell comprising compound F4, measured on an organic optoelectronic component in the form of an organic solar cell.
Figure 6B:
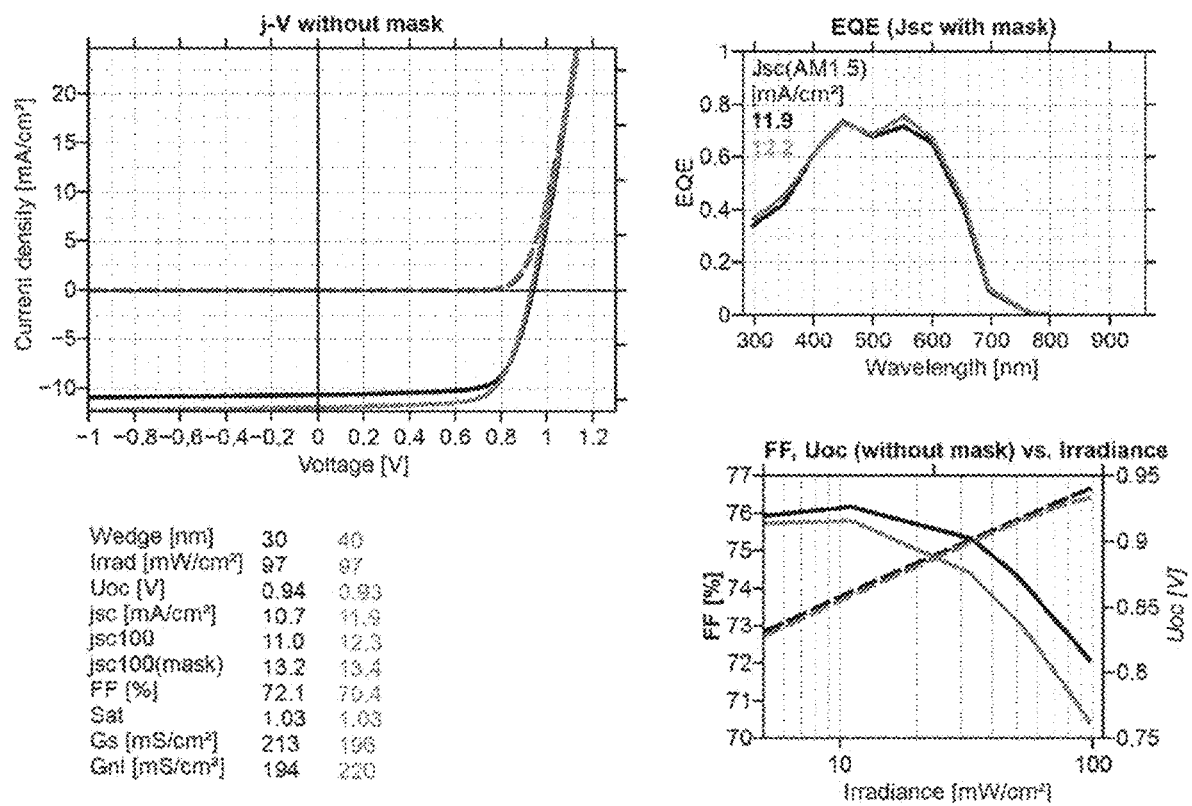

FIG. 6 shows a graph representation of the absorption spectrum of compound F4 (A), and of the current-voltage curve, of a spectral external quantum yield, and of the fill factor of a BHJ cell comprising compound F4, measured on an organic optoelectronic component in the form of an organic solar cell (B).

The current-voltage curve of a BHJ cell having the structure: ITO/C60 (15 nm)/F4: C60 (30 nm, 3:2, 50° C.)/BPAPF (10 nm)/BPAPF:NDP9 (30 nm, 10% by weight NDP9)/NDP9 (1 nm)/Al (100 nm) was determined, with a bulk heterojunction (BHJ) as the photoactive layer. In the optoelectronic component comprising compound F4, the fill factor FF is 72.1%, the open-circuit voltage Uoc is 0.94 V, and the short-circuit current Jsc is 11.9 mA/cm2. The cell efficiency of an optoelectronic component of this type, especially a solar cell, comprising compound F4 is 8.07%.

Figure 7A:
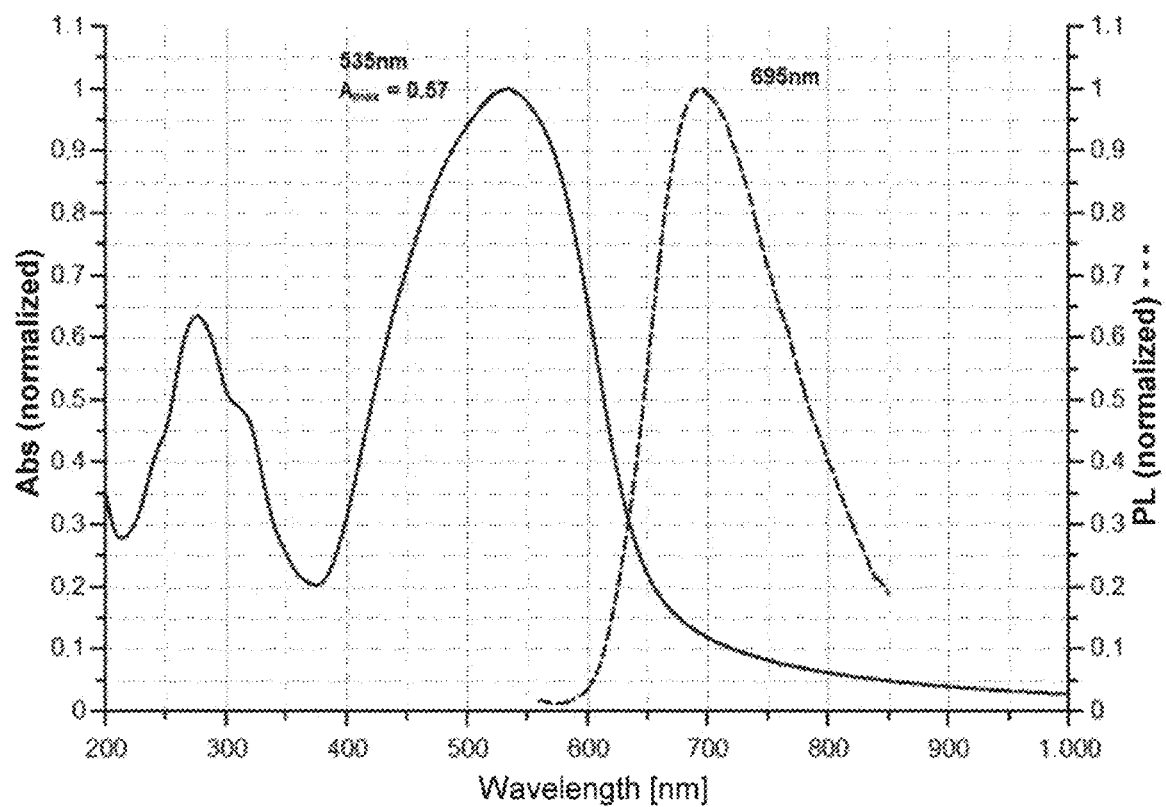
FIG. 7 a graph representation of the absorption spectrum of compound F5, and of the current-voltage curve, of a spectral external quantum yield, and of the fill factor of a BHJ cell comprising compound F5, measured on an organic optoelectronic component in the form of an organic solar cell.
Figure 7B:
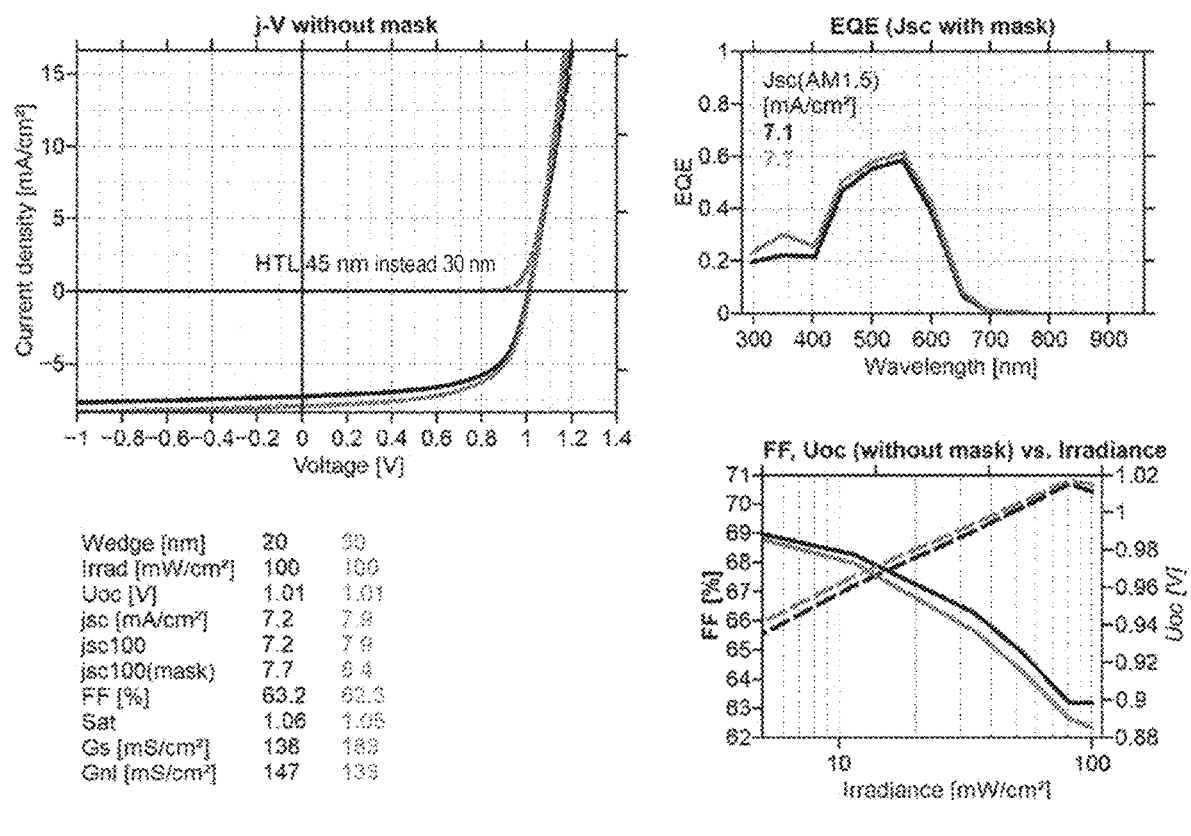

FIG. 7 shows a graph representation of the absorption spectrum of compound F5 (A), and of the current-voltage curve, of a spectral external quantum yield, and of the fill factor of a BHJ cell comprising compound F5, measured on an organic optoelectronic component in the form of an organic solar cell (B).

The current-voltage curve of a BHJ cell having the structure: ITO/C60 (15 nm)/F5:C60 (30 nm, 3:2, 50° C.)/BPAPF (10 nm)/BPAPF:NDP9 (30 nm, 10% by weight NDP9)/NDP9 (1 nm)/Al (100 nm) was determined, with a bulk heterojunction (BHJ) as the photoactive layer. In the optoelectronic component comprising compound F5, the fill factor FF is 62.3%, the open-circuit voltage Uoc is 1.01 V, and the short-circuit current Jsc is 7.7 mA/cm2. The cell efficiency of an optoelectronic component of this type, especially a solar cell, comprising compound F5 is 4.85%.

Figure 8A:
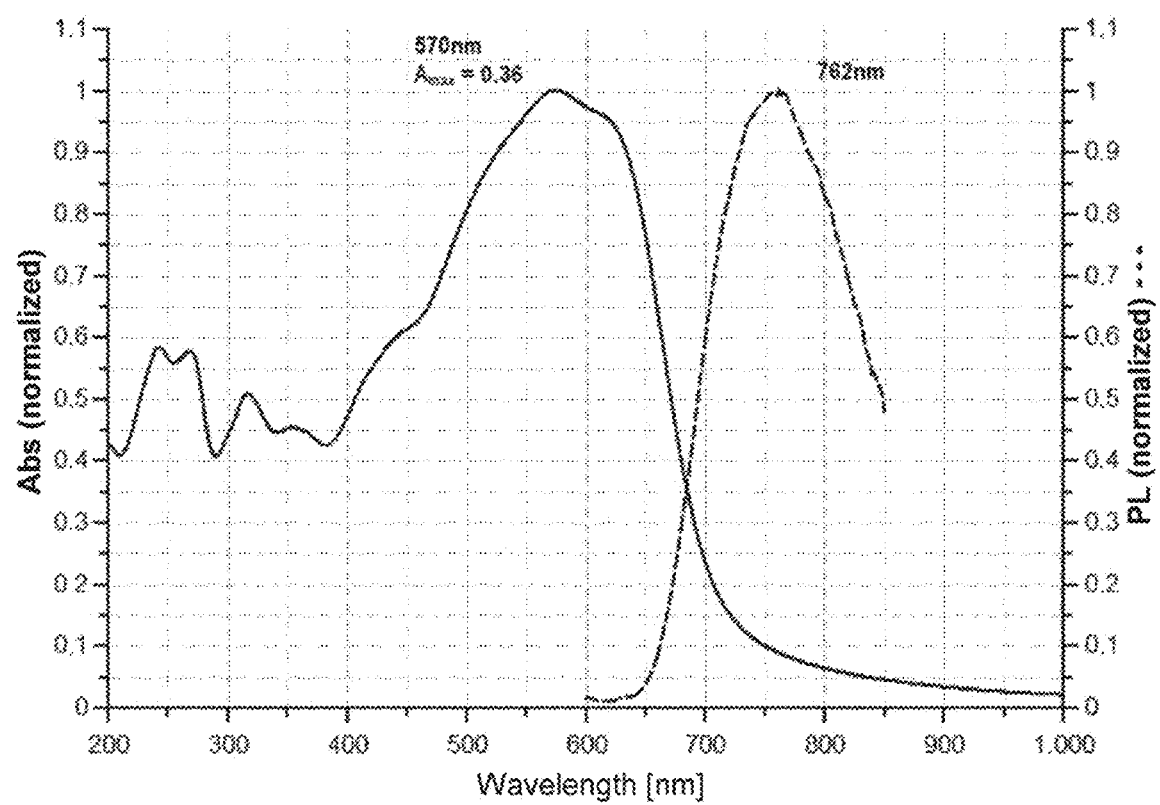
FIG. 8 a graph representation of the absorption spectrum of compound F6, and of the current-voltage curve, of a spectral external quantum yield, and of the fill factor of a BHJ cell comprising compound F6, measured on an organic optoelectronic component in the form of an organic solar cell.
Figure 8B:
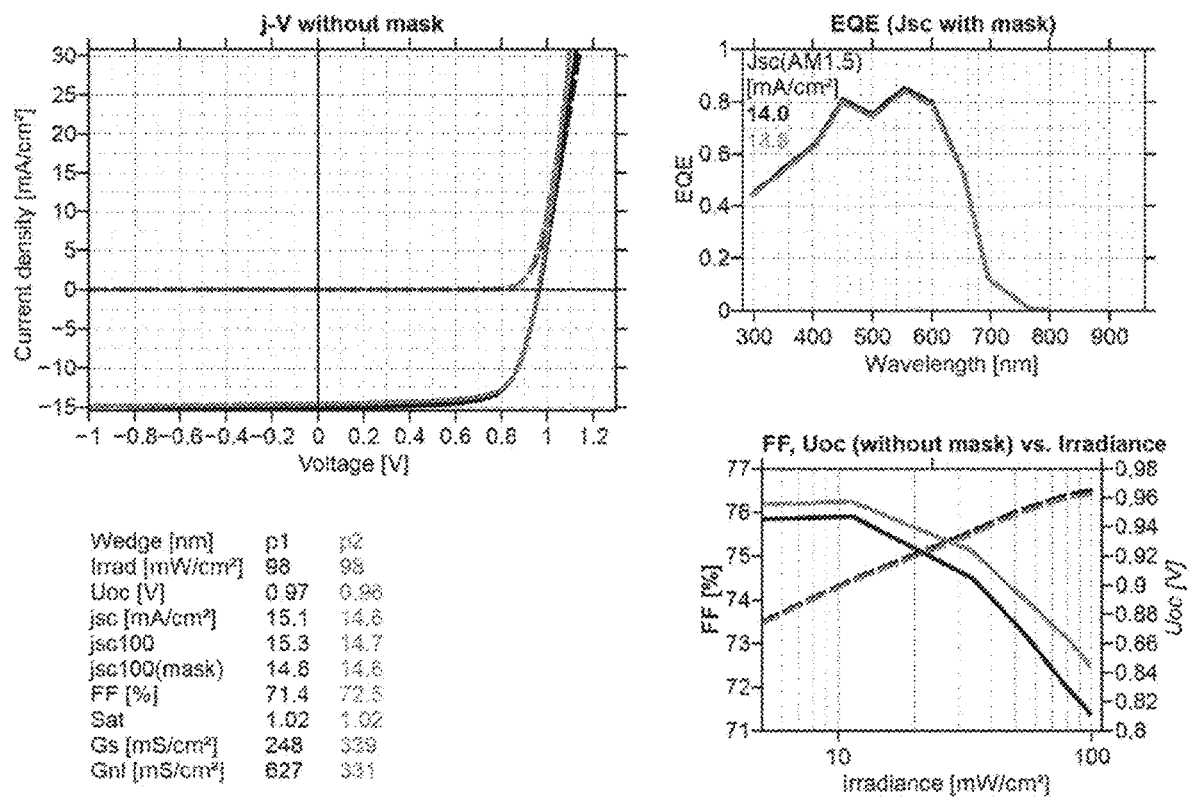
Figure 9A:
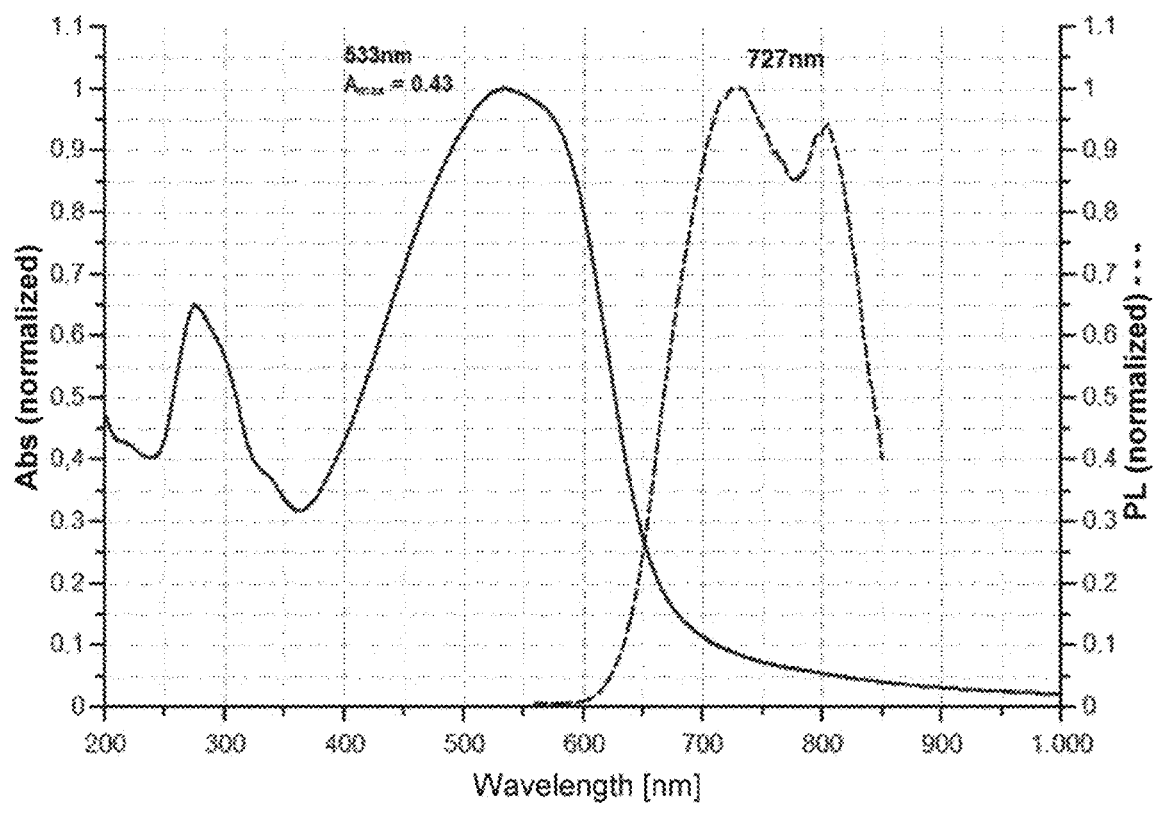
FIG. 9 a graph representation of the absorption spectrum of compound F7, and of the current-voltage curve, of a spectral external quantum yield, and of the fill factor of a BHJ cell comprising compound F7, measured on an organic optoelectronic component in the form of an organic solar cell.
Figure 9B:
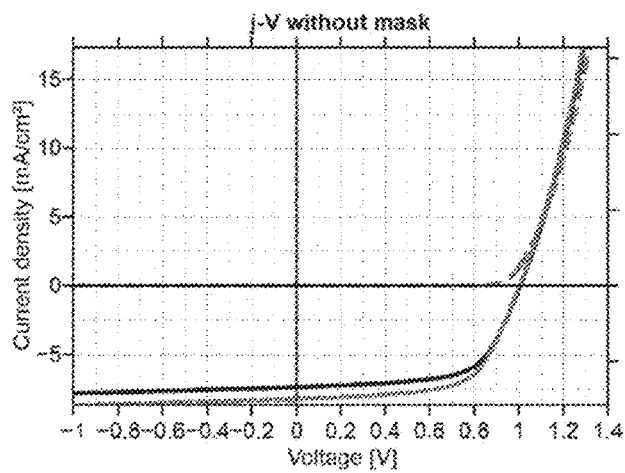
Figure 9B:
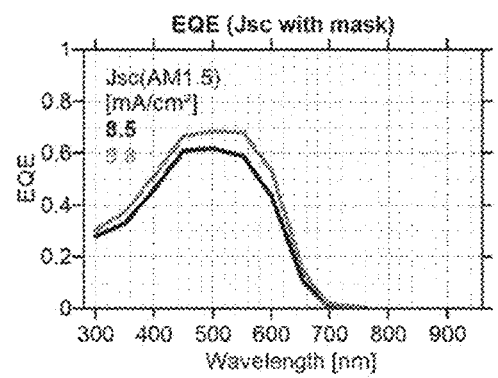
Figure 9B:
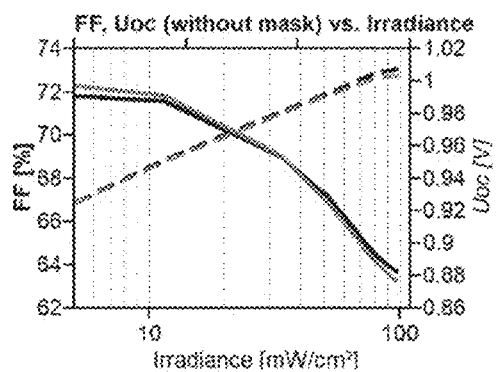
Figure 10A:
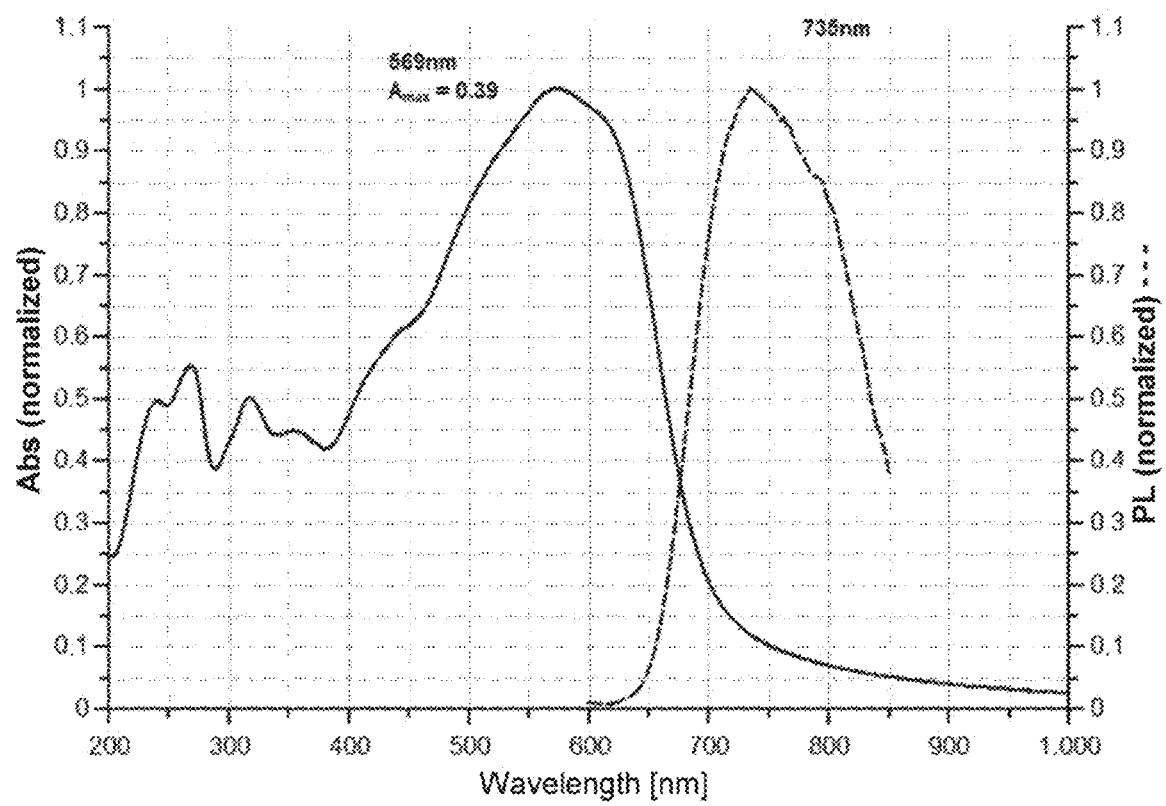
FIG. 10 a graph representation of the absorption spectrum of compound F8, and of the current-voltage curve, of a spectral external quantum yield, and of the fill factor of a BHJ cell comprising compound F8, measured on an organic optoelectronic component in the form of an organic solar cell.
Figure 10B:
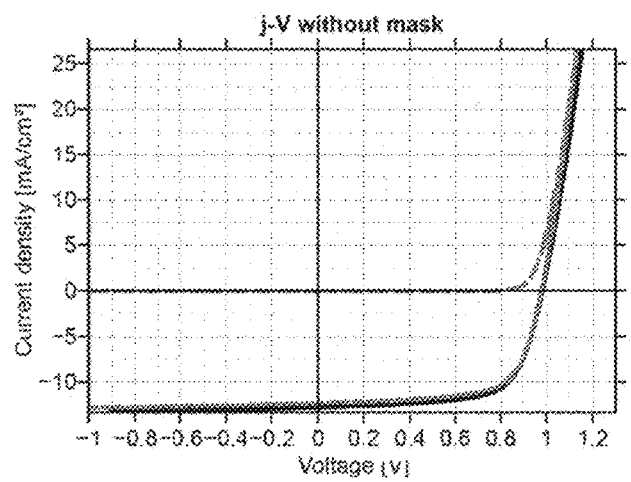
Figure 10B:
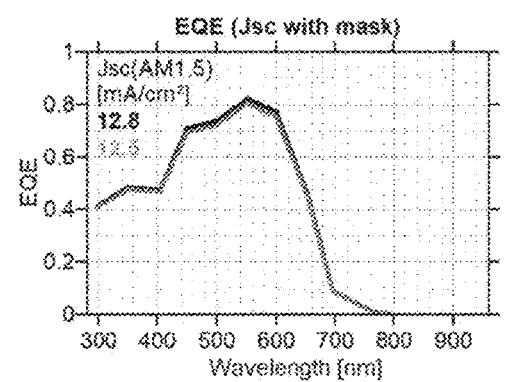
Figure 10B:
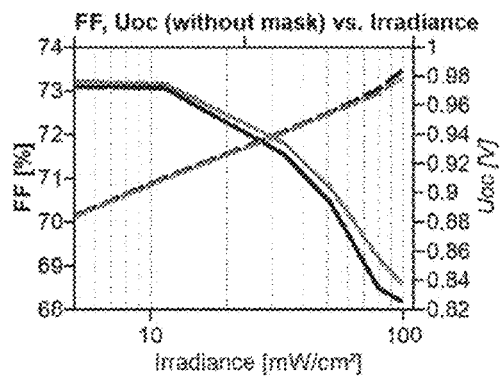
Figure 11A:
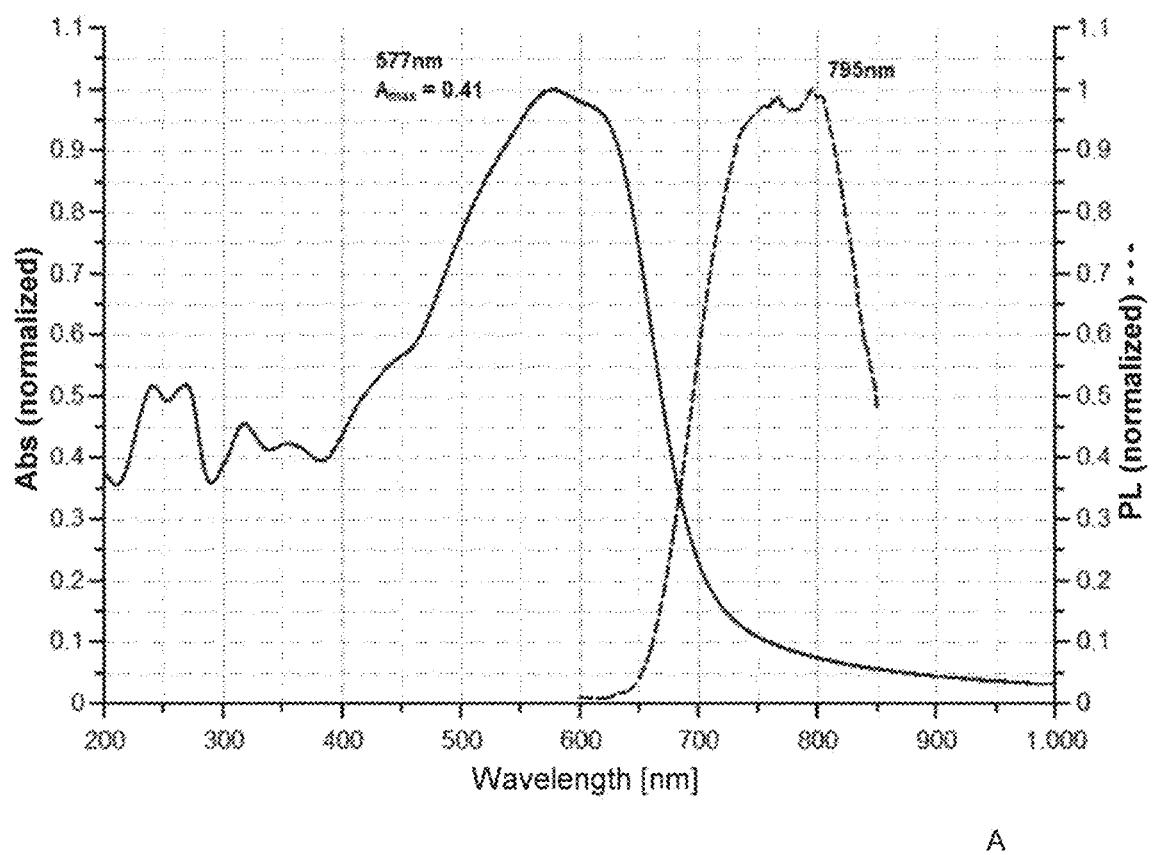
FIG. 11 a graph representation of the absorption spectrum of compound F9, and of the current-voltage curve, of a spectral external quantum yield, and of the fill factor of a BHJ cell comprising compound F9, measured on an organic optoelectronic component in the form of an organic solar cell.
Figure 11B:
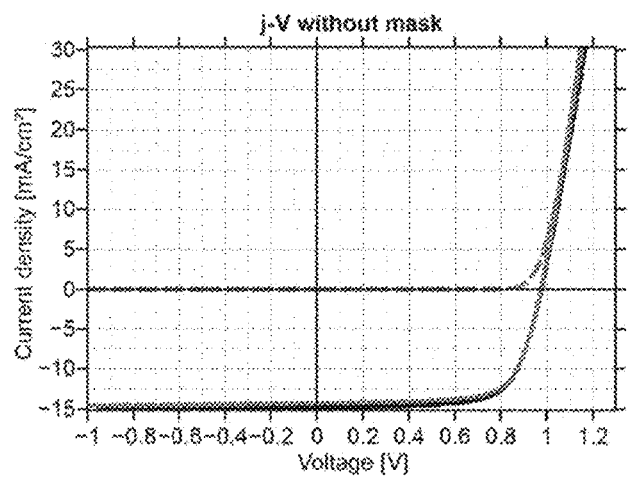
Figure 11B:
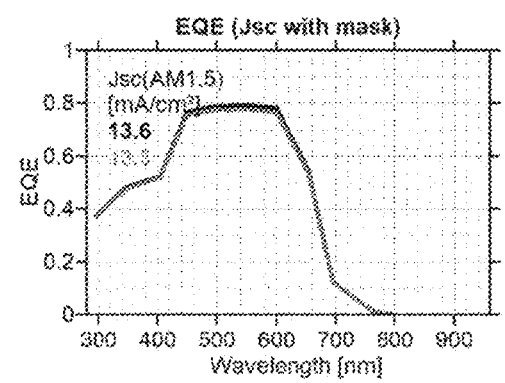
Figure 11B:
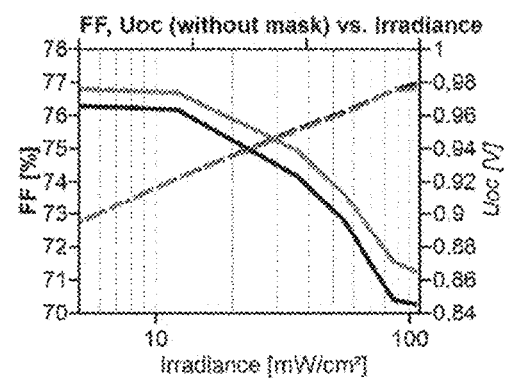

FIG. 8 shows a graph representation of the absorption spectrum of compound F6 (A), and of the current-voltage curve, of a spectral external quantum yield, and of the fill factor of a BHJ cell comprising compound F6, measured on an organic optoelectronic component in the form of an organic solar cell (B).

The current-voltage curve of a BHJ cell having the structure: ITO/C60 (15 nm)/compound F6:C60 (30 nm, 3:2, 50° C.)/BPAPF (10 nm)/BPAPF:NDP9 (30 nm, 10% by weight NDP9)/NDP9 (1 nm)/Al (100 nm) was determined, with a bulk heterojunction (BHJ) as the photoactive layer. In an optoelectronic component comprising compound F6, the fill factor FF is 72.5%, the open-circuit voltage Uoc is 0.96 V, and the short-circuit current Jsc is 13.8 mA/cm2. The cell efficiency of an optoelectronic component of this type, especially a solar cell, comprising compound F6 is 9.60%.

FIG. 9 shows a graph representation of the absorption spectrum of compound F7 (A), and of the current-voltage curve, of a spectral external quantum yield, and of the fill factor of a BHJ cell comprising compound F7, measured on an organic optoelectronic component in the form of an organic solar cell (B).

The current-voltage curve of a BHJ cell having the structure: ITO/C60 (15 nm)/F7:C60 (30 nm, 3:2, 50° C.)/BPAPF (10 nm)/BPAPF:NDP9 (30 nm, 10% by weight NDP9)/NDP9 (1 nm)/Al (100 nm) was determined, with a bulk heterojunction (BHJ) as the photoactive layer. In the optoelectronic component comprising compound F7, the fill factor FF is 63.6%, the open-circuit voltage Uoc is 1.0 V, and the short-circuit current Jsc is 9.8 mA/cm2. The cell efficiency of an optoelectronic component of this type, especially a solar cell, comprising compound F1 is 6.23%.

FIG. 10 shows a graph representation of the absorption spectrum of compound F8 (A), and of the current-voltage curve, of a spectral external quantum yield, and of the fill factor of a BHJ cell comprising compound F8, measured on an organic optoelectronic component in the form of an organic solar cell (B).

The current-voltage curve of a BHJ cell having the structure: ITO/C60 (15 nm)/F8:C60 (30 nm, 3:2, 50° C.)/BPAPF (10 nm)/BPAPF:NDP9 (30 nm, 10% by weight NDP9)/NDP9 (1 nm)/Al (100 nm) was determined, with a bulk heterojunction (BHJ) as the photoactive layer. In the optoelectronic component comprising compound F8, the fill factor FF is 67.9%, the open-circuit voltage Uoc is 0.98 V, and the short-circuit current Jsc is 12.8 mA/cm2. The cell efficiency of an optoelectronic component of this type, especially a solar cell, comprising compound F8 is 8.52%. Compound F8 shows particularly stable behavior under vacuum deposition.

FIG. 11 shows a graph representation of the absorption spectrum of compound F9 (A), and of the current-voltage curve, of a spectral external quantum yield, and of the fill factor of a BHJ cell comprising compound F9, measured on an organic optoelectronic component in the form of an organic solar cell (B).

The current-voltage curve of a BHJ cell having the structure: ITO/C60 (15 nm)/F9:C60 (30 nm, 3:2, 50° C.)/BPAPF (10 nm)/BPAPF:NDP9 (30 nm, 10% by weight NDP9)/NDP9 (1 nm)/Al (100 nm) was determined, with a bulk heterojunction (BHJ) as the photoactive layer. In the optoelectronic component comprising compound F9, the fill factor FF is 70.3%, the open-circuit voltage Uoc is 0.98 V, and the short-circuit current Jsc is 13.6 mA/cm2. The cell efficiency of an optoelectronic component of this type, especially a solar cell, comprising compound F9 is 9.37%.

Figure 12A:
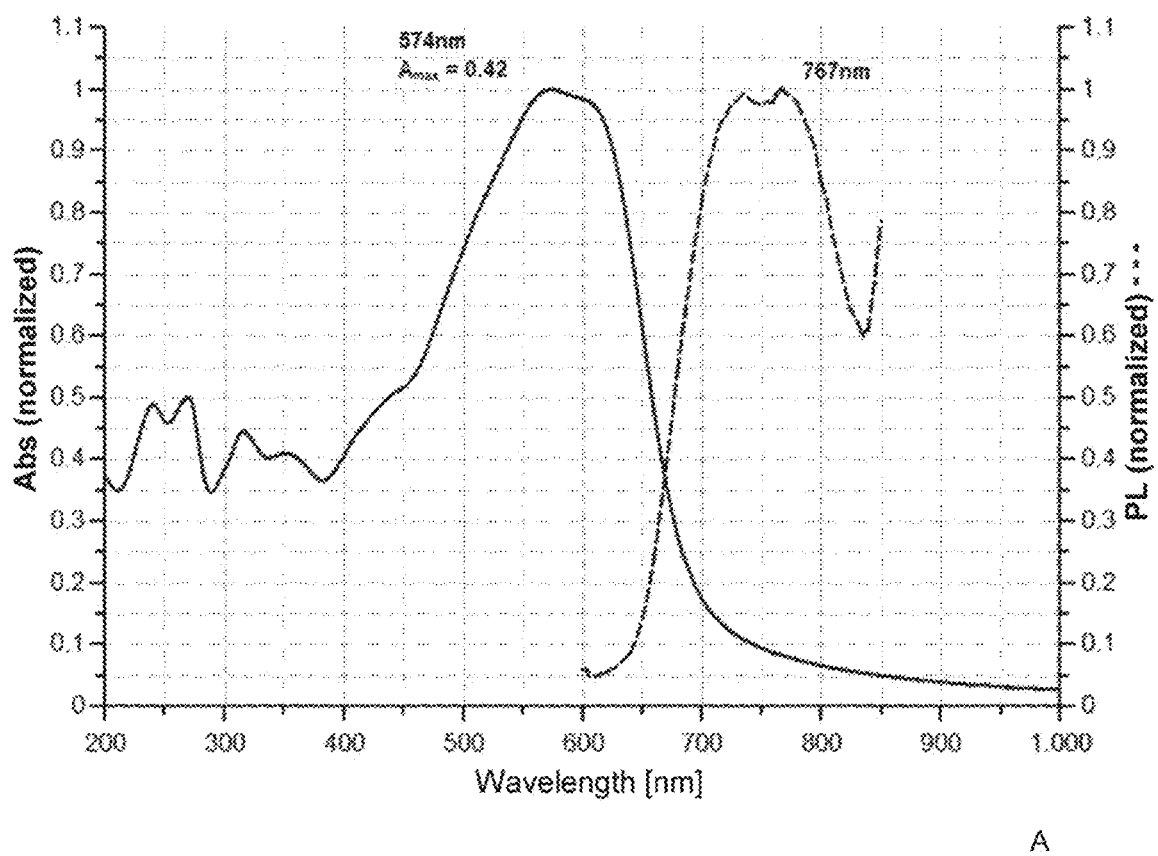
FIG. 12 a graph representation of the absorption spectrum of compound F10, and of the current-voltage curve, of a spectral external quantum yield, and of the fill factor of a BHJ cell comprising compound F10, measured on an organic optoelectronic component in the form of an organic solar cell.
Figure 12B:
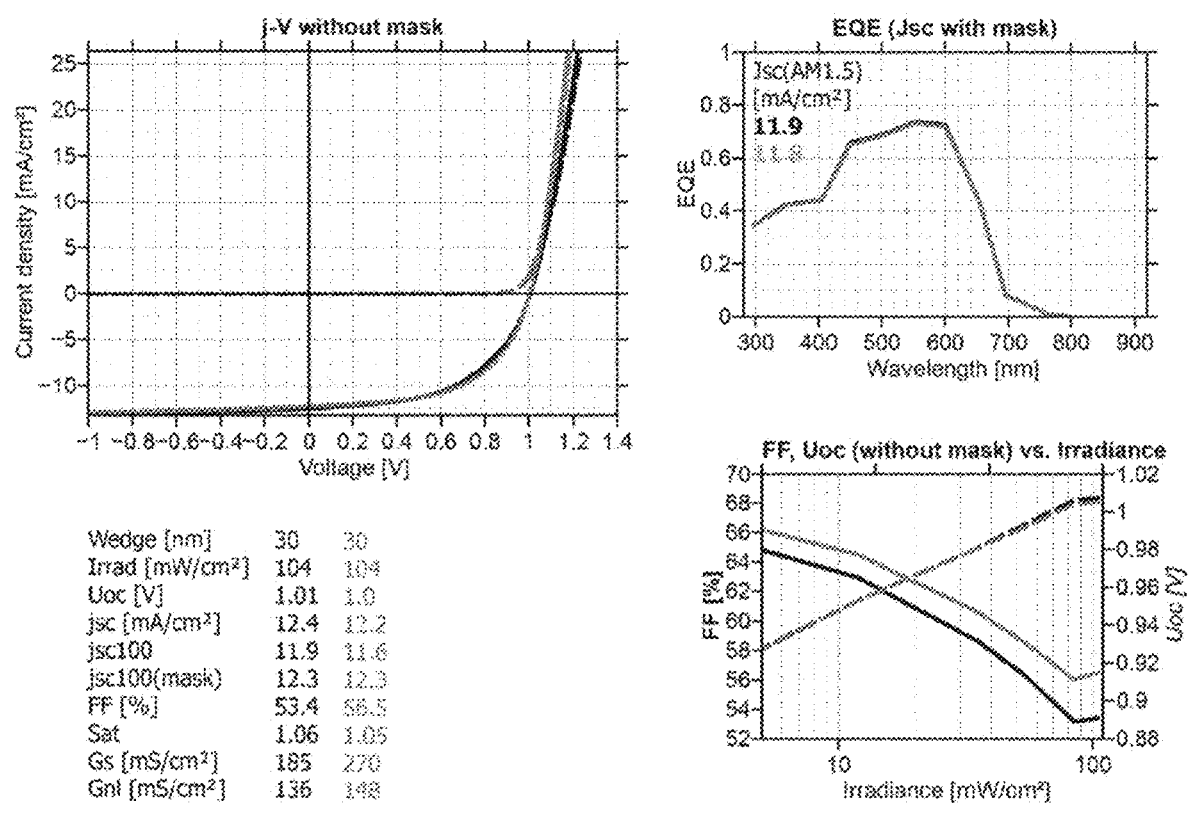
Figure 13A:
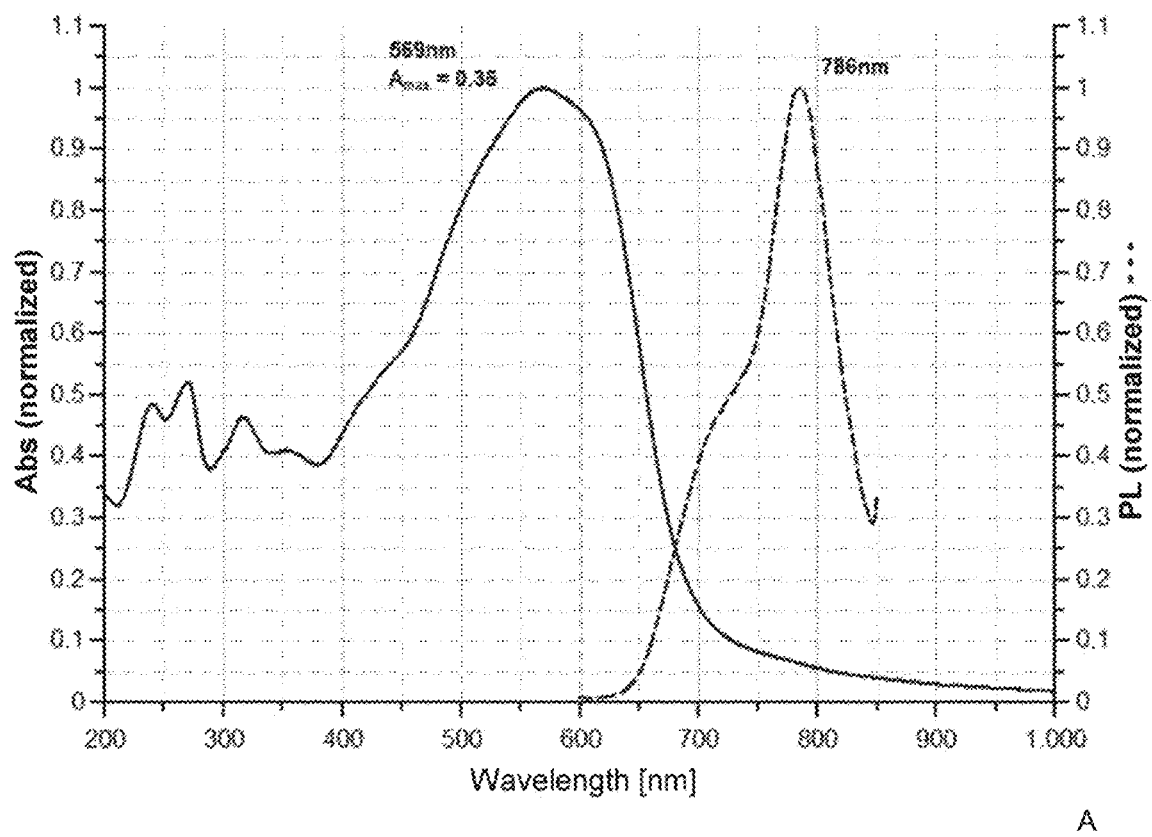
FIG. 13 a graph representation of the absorption spectrum of compound F11, and of the current-voltage curve, of a spectral external quantum yield, and of the fill factor of a BHJ cell comprising compound F11, measured on an organic optoelectronic component in the form of an organic solar cell.
Figure 13B:
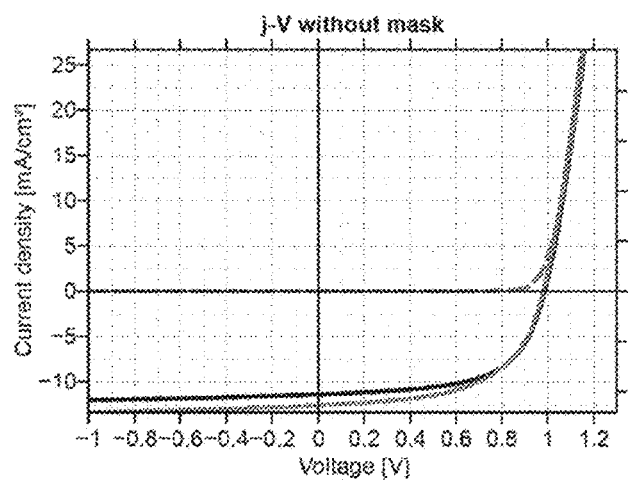
Figure 13B:
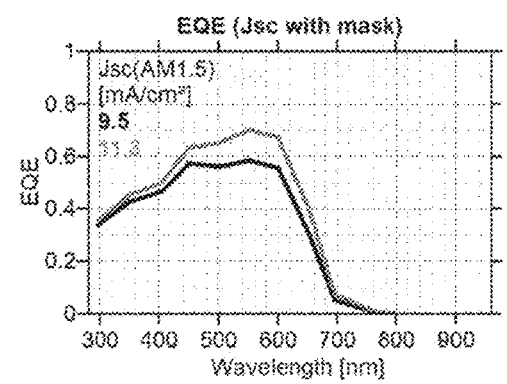
Figure 13B:
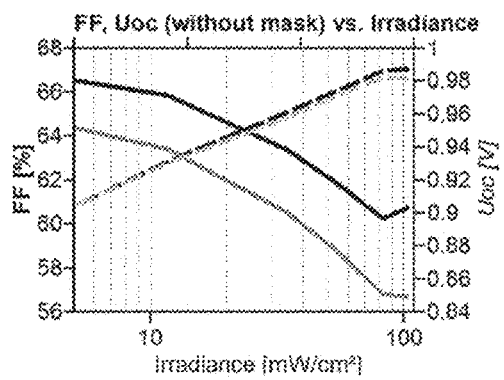

FIG. 12 shows a graph representation of the absorption spectrum of compound F10 (A), and of the current-voltage curve, of a spectral external quantum yield, and of the fill factor of a BHJ cell comprising compound F10, measured on an organic optoelectronic component in the form of an organic solar cell (B).

The current-voltage curve of a BHJ cell having the structure: ITO/C60 (15 nm)/F10:C60 (30 nm, 3:2, 50° C.)/BPAPF (10 nm)/BPAPF:NDP9 (30 nm, 10% by weight NDP9)/NDP9 (1 nm)/Al (100 nm) was determined, with a bulk heterojunction (BHJ) as the photoactive layer. In the optoelectronic component comprising compound F10, the fill factor FF is 56.5%, the open-circuit voltage Uoc is 1.01 V, and the short-circuit current Jsc is 11.8 mA/cm2. The cell efficiency of an optoelectronic component of this type, especially a solar cell, comprising compound F1 is 6.73%.

FIG. 13 shows a graph representation of the absorption spectrum of compound F11 (A), and of the current-voltage curve, of a spectral external quantum yield, and of the fill factor of a BHJ cell comprising compound F11, measured on an organic optoelectronic component in the form of an organic solar cell (B).

The current-voltage curve of a BHJ cell having the structure: ITO/C60 (15 nm)/F11:C60 (30 nm, 3:2, 50° C.)/BPAPF (10 nm)/BPAPF:NDP9 (30 nm, 10% by weight NDP9)/NDP9 (1 nm)/Al (100 nm) was determined, with a bulk heterojunction (BHJ) as the photoactive layer. In the optoelectronic component comprising compound F11, the fill factor FF is 56.7%, the open-circuit voltage Uoc is 0.98 V, and the short-circuit current Jsc is 11.3 mA/cm2. The cell efficiency of an optoelectronic component of this type, especially a solar cell, comprising compound F11 is 6.28%.

Figure 14A:
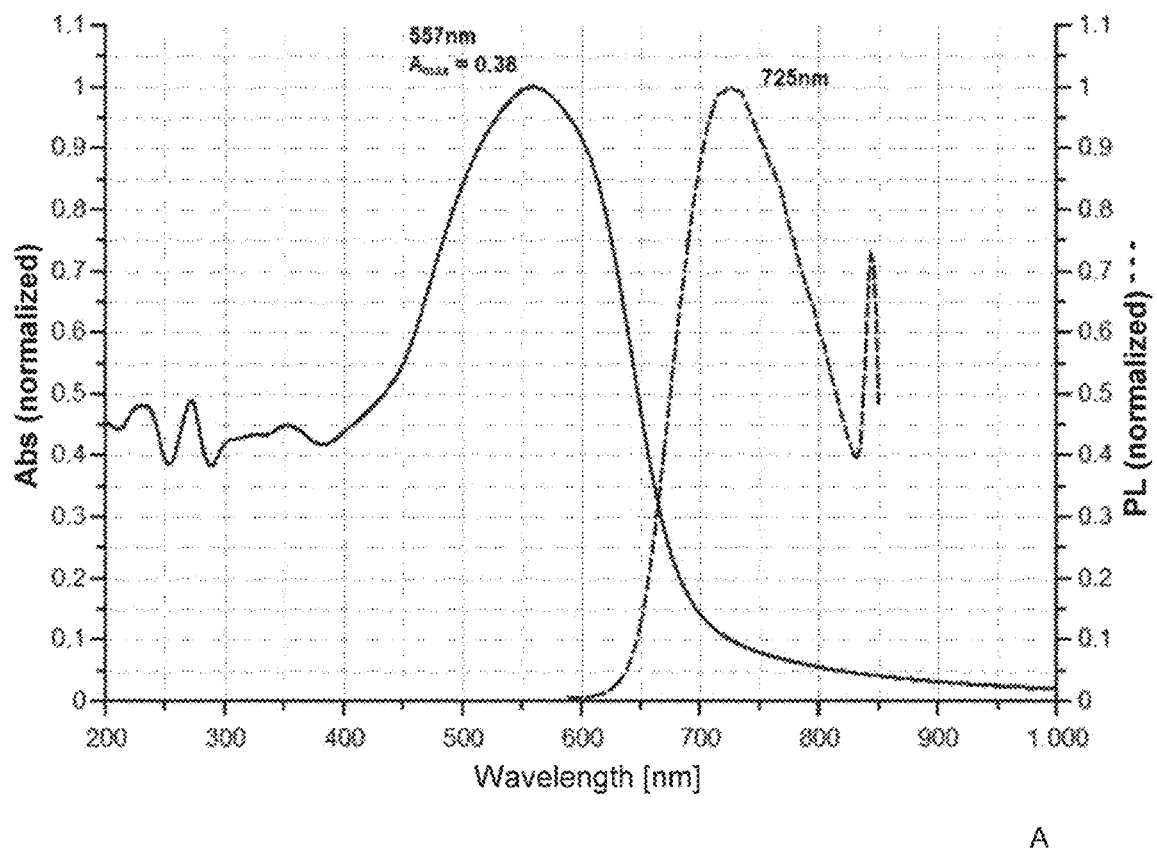
FIG. 14 a graph representation of the absorption spectrum of compound F12, and of the current-voltage curve, of a spectral external quantum yield, and of the fill factor of a BHJ cell comprising compound F12, measured on an organic optoelectronic component in the form of an organic solar cell.
Figure 14B:
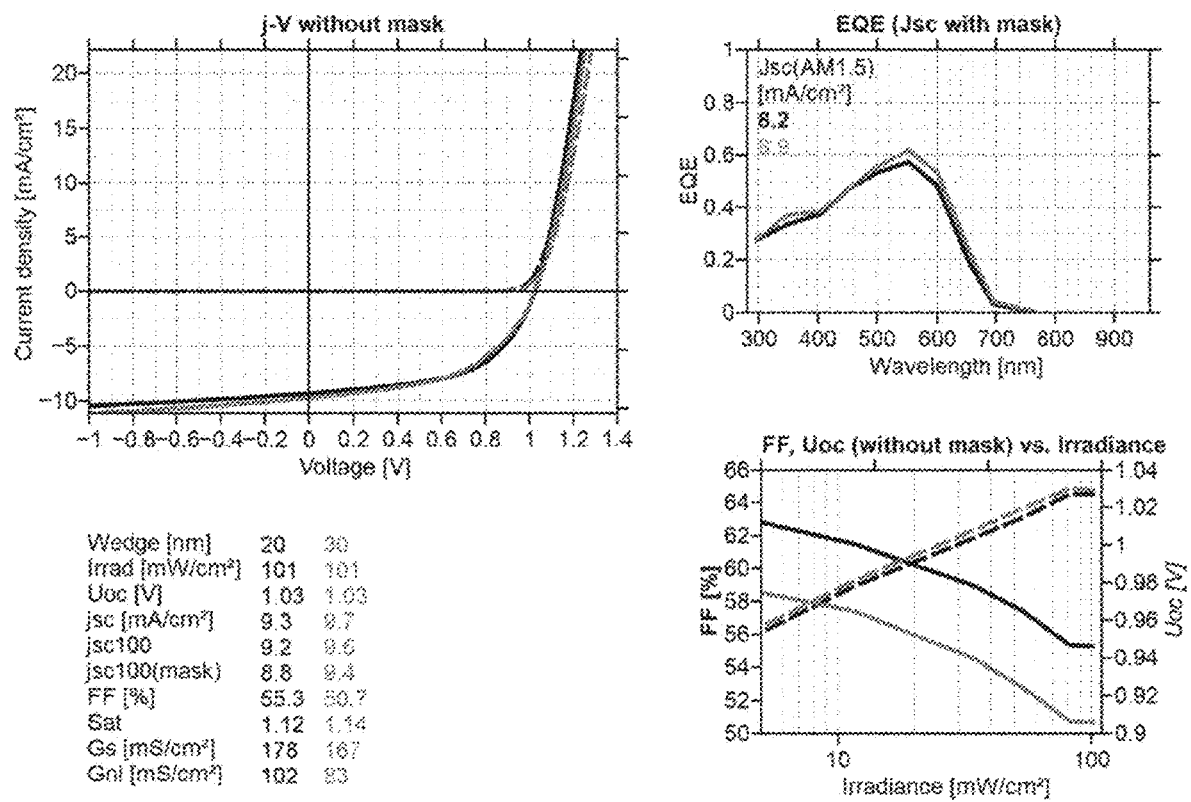

FIG. 14 shows a graph representation of the absorption spectrum of compound F12 (A), and of the current-voltage curve, of a spectral external quantum yield, and of the fill factor of a BHJ cell comprising compound F12, measured on an organic optoelectronic component in the form of an organic solar cell (B).

The current-voltage curve of a BHJ cell having the structure: ITO/C60 (15 nm)/F12:C60 (30 nm, 3:2, 50° C.)/BPAPF (10 nm)/BPAPF:NDP9 (30 nm, 10% by weight NDP9)/NDP9 (1 nm)/Al (100 nm) was determined, with a bulk heterojunction (BHJ) as the photoactive layer. In the optoelectronic component comprising compound F12, the fill factor FF is 50.7%, the open-circuit voltage Uoc is 1.03 V, and the short-circuit current Jsc is 8.9 mA/cm2. The cell efficiency of an optoelectronic component of this type, especially a solar cell, comprising compound F12 is 4.65%.

Figure 15:
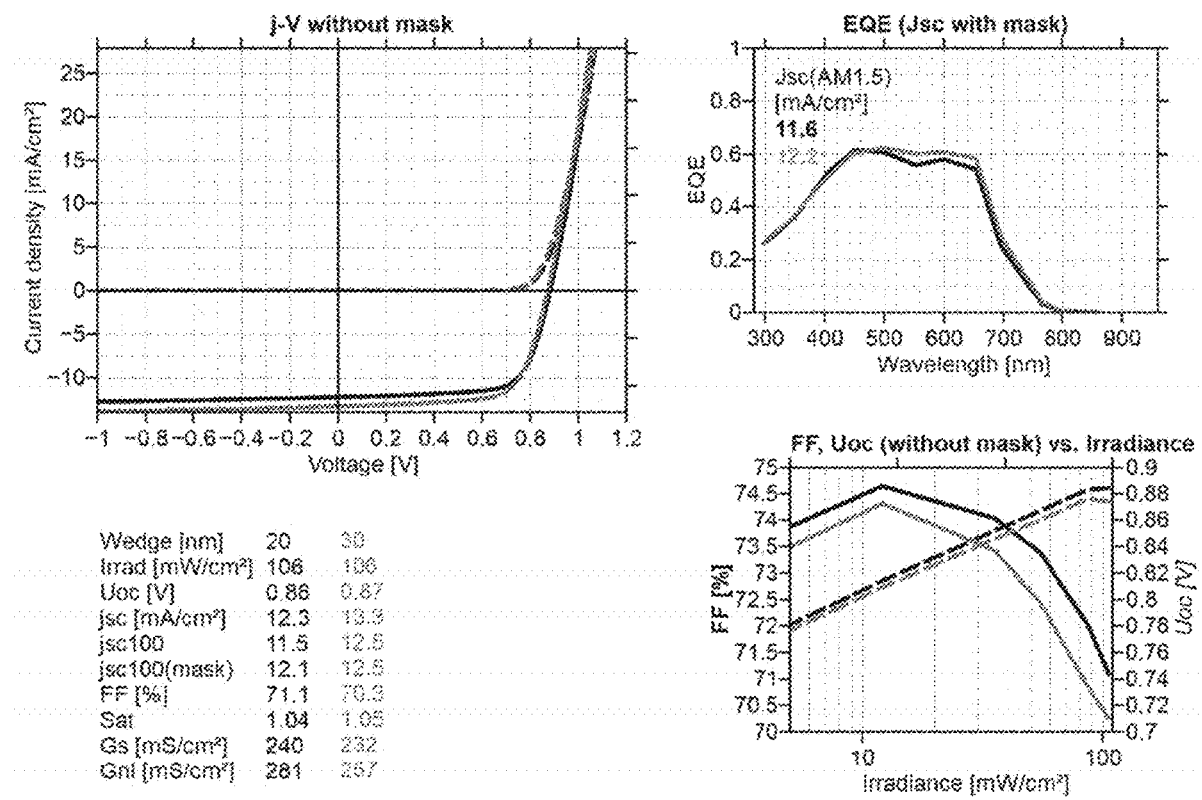
FIG. 15 a graph representation of the current-voltage curve of a spectral external quantum yield, and of the fill factor of a BHJ cell comprising compound F13, measured on an organic optoelectronic component in the form of an organic solar cell.

FIG. 15 shows a graph representation of a spectral external quantum yield and of the fill factor of a BHJ cell comprising compound F13, measured on an organic optoelectronic component in the form of an organic solar cell.

The current-voltage curve of a BHJ cell having the structure: ITO/C60 (15 nm)/F13:C60 (30 nm, 3:2, 50° C.)/BPAPF (10 nm)/BPAPF:NDP9 (30 nm, 10% by weight NDP9)/NDP9 (1 nm)/Al (100 nm) was determined, with a bulk heterojunction (BHJ) as the photoactive layer. In the optoelectronic component comprising compound F13, the fill factor FF is 70.3%, the open-circuit voltage Uoc is 0.87 V, and the short-circuit current Jsc is 12.2 mA/cm2. The cell efficiency of an optoelectronic component of this type, especially a solar cell, comprising compound F13 is 7.46%.

The experimental data of compounds F1 to F13 with the absorption properties of the compounds and the current-voltage curves measured in organic solar cells demonstrate that the compounds of the invention are of very good suitability for use in organic solar cells and other organic optoelectronic components, and especially enable an open-circuit voltage Uoc of more than 0.9 V.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A compound of the general formula I

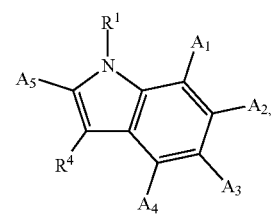

wherein
R1 is selected from the group consisting of H, alkoxy, alkyl, fluorinated alkyl, partly fluorinated alkyl, and aryl;
R4 is selected from the group consisting of H, halogen, CN, alkoxy, alkyl, fluorinated alkyl, partly fluorinated alkyl, branched or linear, cyclic or open-chain alkyl, amino, aryl, and alkenyl;
at least one A1, A2, A3 or A4 in each case is independently the group Ia

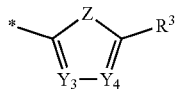

where, in each case, * denotes the attachment to the compound of the general formula I;
Z is selected from the group consisting of O, S, Se, and N—R8 where R8 is selected from the group consisting of H, alkoxy, alkyl, fluorinated alkyl, partly fluorinated alkyl, and aryl;
Y3 is N or C—R9 where R9 is selected from the group consisting of H, halogen, alkoxy, branched or linear, cyclic or open chain alkyl, alkenyl, and aryl, wherein H may in each case be substituted;
Y4 is N or C-10 where R10 is selected from the group consisting of H, halogen, alkoxy, branched or linear, cyclic or open-chain alkyl, alkenyl, and aryl, wherein H may in each case be substituted;
where R9 and R10 may be bonded homocyclically or heterocyclically to one another in the form of a ring structure; and
R3 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double done, wherein H may be substituted by CN or F;
the other A1, A2, A3 or A4 are each independently selected from the group consisting of H, halogen, CN, alkoxy, alkyl, fluorinated alkyl, partly fluorinated alkyl, and amino; and
A5 is the group Ib

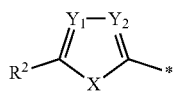

where * denotes the attachment to the compound of the general formula I;
X is selected from the group consisting of O, S, Se, and N—R7, where R7 is selected from the group consisting of H, alkoxy, alkyl, fluorinated alkyl, partly fluorinated alkyl, and aryl;
Y1 is N or C—R5 where R5 is selected from the group consisting of H, halogen, alkoxy, branched or linear, cyclic or open-chain alkyl, alkenyl, and aryl, wherein H may in each case be substituted;
Y2 is N or C—R6 where R6 is selected from the group consisting of H, halogen, alkoxy, branched or linear, cyclic or open-chain alkyl, alkenyl, and aryl, wherein H may in each case be substituted;
where R5 and R6 may be bonded homocyclically or heterocyclically to one another in the form of a ring structure; and R2 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double bond, wherein H may be substituted by CN or F.

2. The compound of claim 1, wherein the compound is a compound of the general formula II

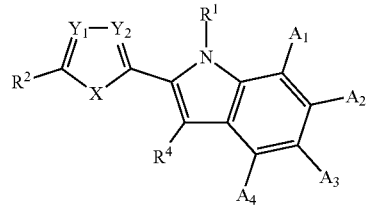

where R1 optionally is selected from the group consisting of H and alkyl;
R4 optionally is selected from the group consisting of H, halogen, CN, alkoxy and alkyl; and
where X and Z are each independently O or S.

3. The compound of claim 1, wherein the compound is a compound of the general formula VII

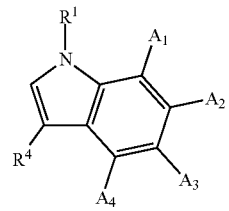

where R1 optionally is selected from the group consisting of H, methyl, ethyl, propyl, isopropyl, butyl, isobutyl and s-butyl;
R4 optionally is selected from the group consisting of H, halogen, CN, alkoxy and alkyl; and
where Z is O or S.

4. The compound of claim 1, wherein at least one A1, A2, A3 or A4 in each case is independently a

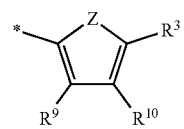

where R3 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double bond, wherein H may be substituted by CN or F;
R9 is selected from the group consisting of H, halogen, alkoxy, branched or linear, cyclic or open-chain alkyl, alkenyl, aryl, wherein H may in each case be substituted;
R10 is selected from the group consisting of H, halogen, alkoxy, branched or linear, cyclic or open-chain alkyl, alkenyl, and aryl, wherein H may in each case be substituted; and
where R9 and R10 may be homocyclically or heterocyclically linked to one another in the form of a ring structure.

5. The compound of claim 1, wherein the compound is a compound of the general formulae III and/or IV

III

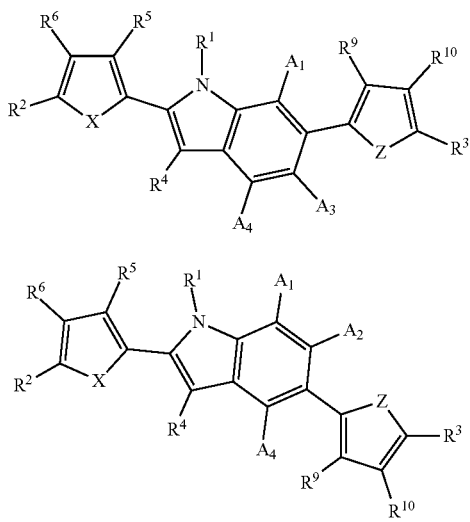

IV where R1 is selected from the group consisting of H, methyl, ethyl, propyl, isopropyl, butyl, isobutyl and s-butyl;

X and Z are each independently O or S;

A1, A3 and A4, or A1, A2 and A4, are each independently selected from the group consisting of H, halogen, CN, alkoxy, alkyl, fluorinated alkyl, and partly fluorinated alkyl;

R3 is selected from the group consisting of H, alkyl, fluorinated alkyl, partly fluorinated alkyl, alkoxy, amino, aryl, and an electron-withdrawing alkyl group having at least one C—C double bond, wherein H may be substituted by CN or F; and where, optionally, X and Z are O, R4 is H, and R5 and R6 are H.

6. The compound of claim 1, wherein, in formula III, A1, A3 and A4 are H (formula V), and, in formula IV, A1, A2 and A4 are H (formula VI),

V

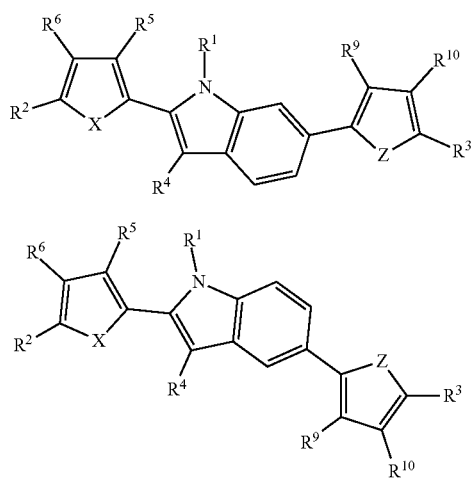

VI where X and Z are each independently O or S;
where R5 and R6 optionally are H.

7. The compound of claim 1, wherein the compound is a compound of general formula X:

X

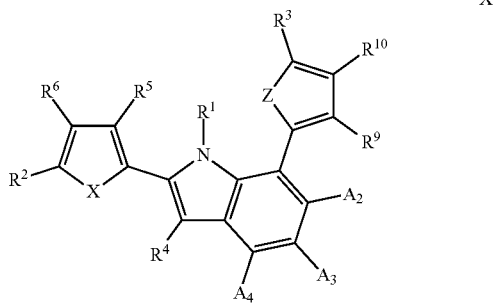

where R1 is H or alkyl;

X and Z are each independently O or S;

A2, A3 and A4 are each independently selected from the group consisting of H, halogen, CN, alkoxy, alkyl, fluorinated alkyl, and partly fluorinated alkyl;

R3 is selected from the group consisting of H, alkyl, fluorinated alkyl, partly fluorinated alkyl, alkoxy, amino, aryl, and an electron-withdrawing alkyl group having at least one C—C double bond, wherein H may be substituted by CN or F; and where, optionally, X and Z are O, R4 is H, and R5 and R6 are H.

8. The compound of claim 1, wherein the compound is a compound of the general formula XI:

XI

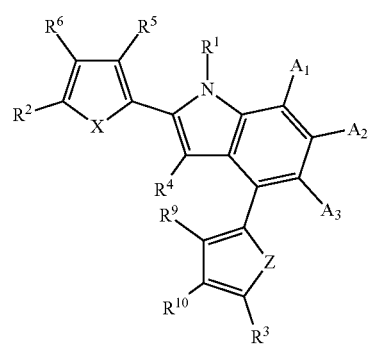

where R1 is H or alkyl;

X and Z are each independently O or S;

A1, A2 and A3 are each independently selected from the group consisting of H, halogen, CN, alkoxy, alkyl, fluorinated alkyl, and partly fluorinated alkyl;

R3 is selected from the group consisting of H, alkyl, fluorinated alkyl, partly fluorinated alkyl, alkoxy, amino, aryl, and an electron-withdrawing alkyl group having at least on C—C double bond, wherein H may be substituted by CN or F; and where, optionally, X and Z are O, R4 is H, and R5 and R6 are H.

9. The compound of claim 1, wherein the compound is a compound of the general formula VIII or IX

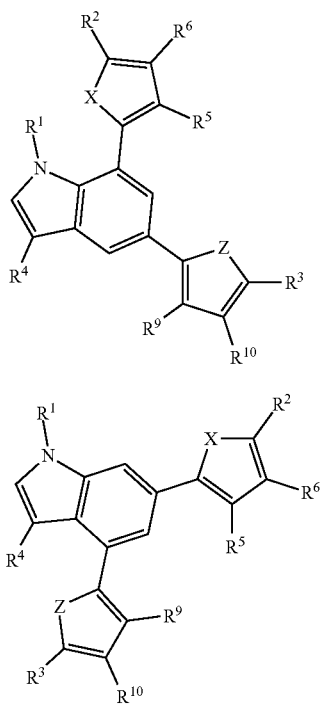

VIII

IX where R1 is H or alkyl;
X and Z are each independently O or S;
R9 is selected from the group consisting of H, halogen, alkoxy, branched or linear, cyclic or open-chain alkyl, alkenyl, and aryl, wherein H may in each case be substituted;
R10 is selected from the group consisting of H, halogen, alkoxy, branched or linear, cyclic or open-chain alkyl, alkenyl, and aryl, wherein H may in each case be substituted; and
where R9 and R10 may be bonded homocyclically or heterocyclically to one another in the form of a ring structure,
R5 is selected from the group consisting of H, halogen, alkoxy, branched or linear, cyclic or open-chain alkyl, alkenyl, and aryl, wherein H may in each case be substituted;
R6 is selected from the group consisting of H, halogen, alkoxy, branched or linear, cyclic or open-chain alkyl, alkenyl, and aryl, wherein H may in each case be substituted; and
where R5 and R6 may be bonded homocyclically or heterocyclically to one another in the form of a ring structure;
where, optionally, R5 and R6 are H and R9 and R10 are H.

10. The compound of claim 1, wherein R2 and R3 are each independently

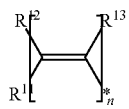

where n is 1, 2, 3 or 4, where * in each case denotes the attachment to the group of the general formula Ia and/or Ib;

R11, R12 and R13 are each independently selected from the group consisting of H, halogen, CN, COO-alkyl, alkenyl, alkynyl, alkoxy, cyclic or open-chain alkyl, cyclic or open-chain alkenyl, where H in each case may be substituted by halogen or CN, provided that R11 and R12 are not both H,
where R11 and R12 optionally are CN.

11. The compound of claim 1, wherein R2 and R3 are each independently selected from the group consisting of:

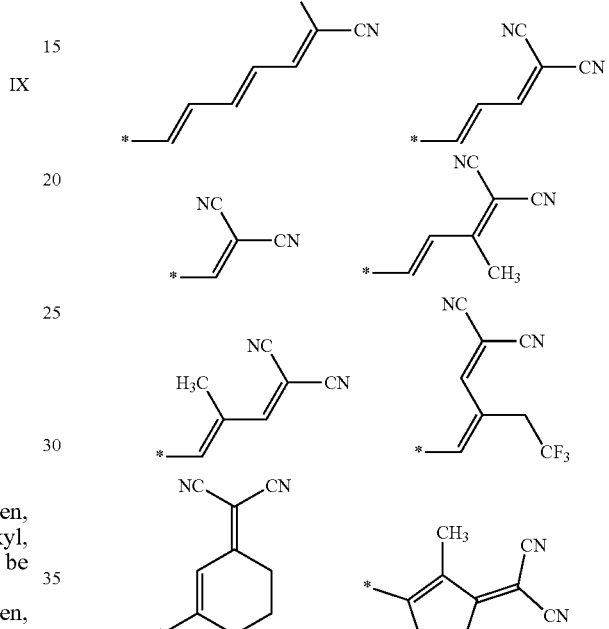

where * denotes the attachment to the group of the general formula Ia and/or Ib, where R2 and R3 optionally are the same.

12. The compound of claim 1, wherein the compound is selected from the group consisting of:

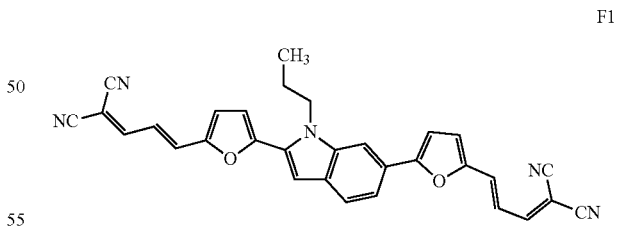

F1

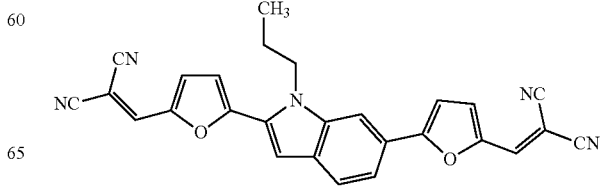

F2

F3
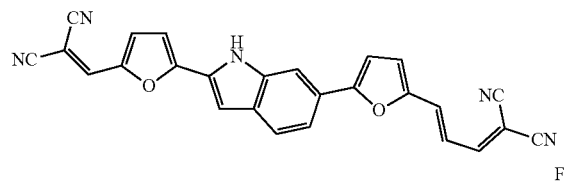

F4
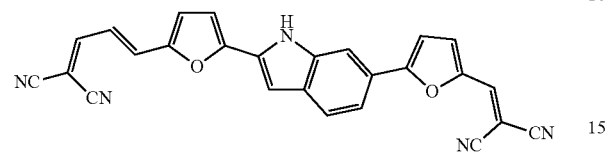

F5
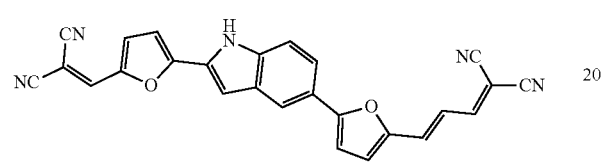

F6
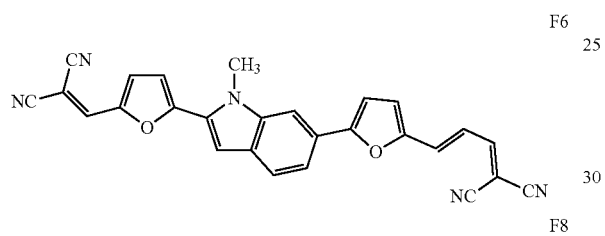

F8
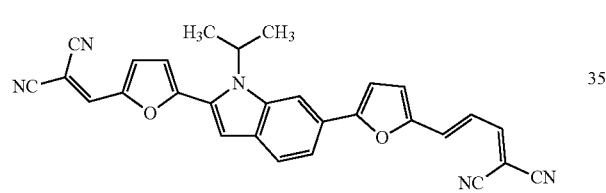

F9
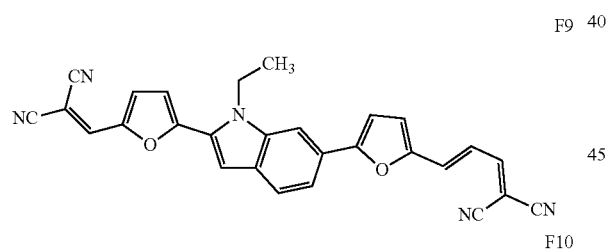

F10
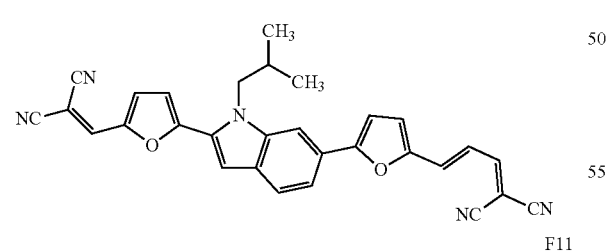

F11
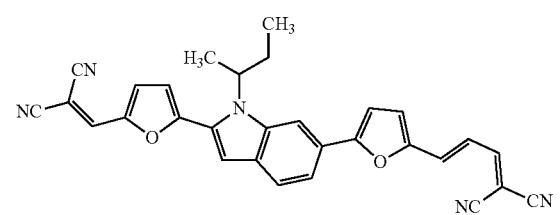

F12
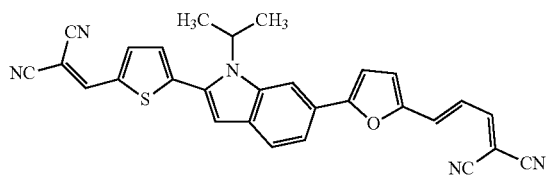

F13
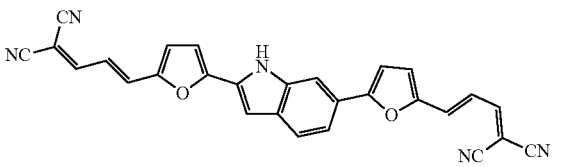

F15
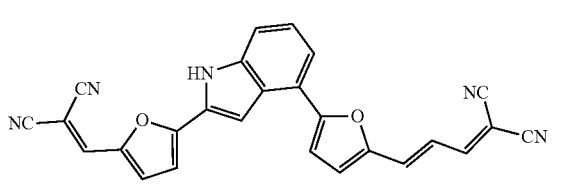

F17
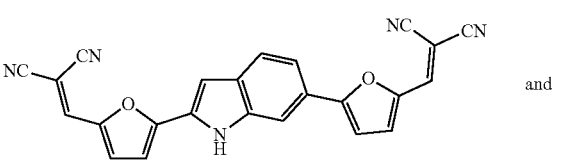

and

F18
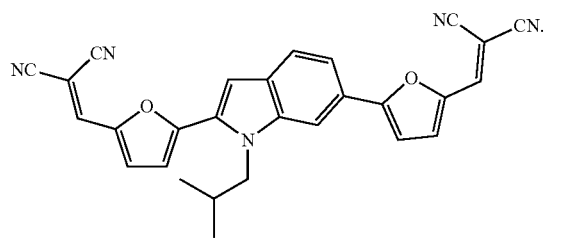

13. An optoelectronic component comprising a first electrode (2), a second electrode (3), and a layer system, with the layer system (7) being arranged between the first electrode (1) and the second electrode (2), characterized in that at least one layer of the layer system (7) includes at least one compound of claim 1, where the optoelectronic component optionally is an organic solar cell, an OFET, and OLED or an organic photodetector.

14. The optoelectronic component of claim 13, wherein the layer system (7) has at least one photoactive layer (4), optionally an absorber layer, with the layer system (7) optionally having at least two photoactive layers, optionally at least three photoactive layers, or optionally at least four photoactive layers.

15. The optoelectronic component of claim 14, wherein the photoactive layer (4) is formed as a mixed layer of:

a compound of the general formula I

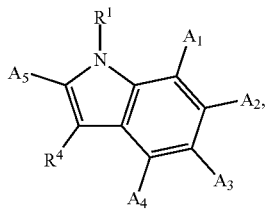

wherein
R1 is selected from the group consisting of H, alkoxy, alkyl, fluorinated alkyl, partly fluorinated alkyl, and aryl;
R4 is selected from the group consisting of H, halogen, CN, alkoxy, alkyl, fluorinated alkyl, partly fluorinated alkyl, branched or linear, cyclic or open-chain alkyl, amino, aryl, and alkenyl;
at least one A1, A2, A3 or A4 in each case is independently the group Ia

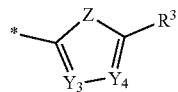

where, in each case, * denotes the attachment to the compound of the general formula I;
Z is selected from the group consisting of O, S, Se, and N—R8 where R8 is selected from the group consisting of H, alkoxy, alkyl, fluorinated alkyl, partly fluorinated alkyl, and aryl;
Y3 is N or C—R9 where R9 is selected from the group consisting of H, halogen, alkoxy, branched or linear, cyclic or open chain alkyl, alkenyl, and aryl, wherein H may in each case be substituted;
Y4 is N or C-10 where R10 is selected from the group consisting of H, halogen, alkoxy, branched or linear, cyclic or open-chain alkyl, alkenyl, and aryl, wherein H may in each case be substituted;
where R9 and R10 may be bonded homocyclically or heterocyclically to one another in the form of a ring structure; and
R3 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double done, wherein H may be substituted by CN or F;
the other A1, A2, A3 or A4 are each independently selected from the group consisting of H, halogen, CN, alkoxy, alkyl, fluorinated alkyl, partly fluorinated alkyl, and amino; and
A5 is the group Ib

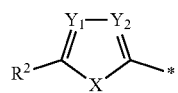

where * denotes the attachment to the compound of the general formula I;
X is selected from the group consisting of O, S, Se, and N—R7, where R7 is selected from the group consisting of H, alkoxy, alkyl, fluorinated alkyl, partly fluorinated alkyl, and aryl;
Y1 is N or C—R5 where R5 is selected from the group consisting of H, halogen, alkoxy, branched or linear, cyclic or open-chain alkyl, alkenyl, and aryl, wherein H may in each case be substituted;
Y2 is N or C—R6 where R6 is selected from the group consisting of H, halogen, alkoxy, branched or linear, cyclic or open-chain alkyl, alkenyl, and aryl, wherein H may in each case be substituted;
where R5 and R6 may be bonded homocyclically or heterocyclically to one another in the form of a ring structure; and R2 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double bond, wherein H may be substituted by CN or F; and
at least one further compound.

16. An organic optoelectronic component comprising at least one compound of claim 1, optionally wherein the organic optoelectronic component is an organic solar cell.

17. The compound of claim 2, wherein R1 is selected from the group consisting of H and alkyl; and R4 is selected from the group consisting of H, halogen, CN, alkoxy and alkyl.

18. The compound of claim 3, wherein where R1 is selected from the group consisting of H, methyl, ethyl, propyl, isopropyl, butyl, isobutyl and s-butyl; and R4 is selected from the group consisting of H, halogen, CN, alkoxy and alkyl.

19. The compound of claim 5, wherein X and Z are O, R4 is H, and R5 and R6 are H.

20. The optoelectronic component of claim 14, wherein the at least one photoactive layer (4) comprises a compound of general formula I

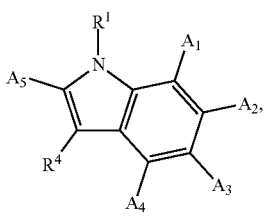

wherein
R1 is selected from the group consisting of H, alkoxy, alkyl, fluorinated alkyl, partly fluorinated alkyl, and aryl;
R4 is selected from the group consisting of H, halogen, CN, alkoxy, alkyl, fluorinated alkyl, partly fluorinated alkyl, branched or linear, cyclic or open-chain alkyl, amino, aryl, and alkenyl;
at least one A1, A2, A3 or A4 in each case is independently the group Ia

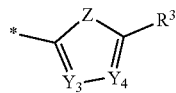

where, in each case, * denotes the attachment to the compound of the general formula I;

Z is selected from the group consisting of O, S, Se, and N—R8 where R8 is selected from the group consisting of H, alkoxy, alkyl, fluorinated alkyl, partly fluorinated alkyl, and aryl;

Y3 is N or C—R9 where R9 is selected from the group consisting of H, halogen, alkoxy, branched or linear, cyclic or open chain alkyl, alkenyl, and aryl, wherein H may in each case be substituted;

Y4 is N or C-10 where R10 is selected from the group consisting of H, halogen, alkoxy, branched or linear, cyclic or open-chain alkyl, alkenyl, and aryl, wherein H may in each case be substituted;

where R9 and R10 may be bonded homocyclically or heterocyclically to one another in the form of a ring structure; and R3 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double done, wherein H may be substituted by CN or F;

the other A1, A2, A3 or A4 are each independently selected from the group consisting of H, halogen, CN, alkoxy, alkyl, fluorinated alkyl, partly fluorinated alkyl, and amino; and A5 is the group Ib

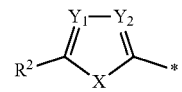

where * denotes the attachment to the compound of the general formula I;

X is selected from the group consisting of O, S, Se, and N—R7, where R7 is selected from the group consisting of H, alkoxy, alkyl, fluorinated alkyl, partly fluorinated alkyl, and aryl;

Y1 is N or C—R5 where R5 is selected from the group consisting of H, halogen, alkoxy, branched or linear, cyclic or open-chain alkyl, alkenyl, and aryl, wherein H may in each case be substituted;

Y2 is N or C—R6 where R6 is selected from the group consisting of H, halogen, alkoxy, branched or linear, cyclic or open-chain alkyl, alkenyl, and aryl, wherein H may in each case be substituted;

where R5 and R6 may be bonded homocyclically or heterocyclically to one another in the form of a ring structure; and R2 is selected from the group consisting of H, alkoxy, alkyl, fluorinated alkyl, partly fluorinated alkyl, branched or linear, cyclic or open-chain alkyl, amino, aryl, alkenyl, and an electron-withdrawing alkyl group having at least one C—C double bond, wherein H may be substituted by CN or F.

* * * * *